(12) United States Patent
Mu et al.

(10) Patent No.: US 7,462,465 B2
(45) Date of Patent: Dec. 9, 2008

(54) NUCLEIC ACID ENCODING KCNB POTASSIUM CHANNEL

(75) Inventors: David Mu, Jericho, NY (US); Scott Powers, Greenlawn, NY (US)

(73) Assignee: Amgen, Inc., Thousand Oaks, CA (US)

( * ) Notice: Subject to any disclaimer, the term of this patent is extended or adjusted under 35 U.S.C. 154(b) by 1741 days.

(21) Appl. No.: 09/798,584

(22) Filed: Mar. 2, 2001

(65) Prior Publication Data

US 2002/0102676 A1 Aug. 1, 2002

Related U.S. Application Data

(60) Provisional application No. 60/186,915, filed on Mar. 3, 2000.

(51) Int. Cl.
  C12N 15/11 (2006.01)
  C12N 15/63 (2006.01)
  C12N 5/10 (2006.01)
(52) U.S. Cl. .................. 435/69.1; 435/320.1; 435/325; 536/23.5
(58) Field of Classification Search ........................ None
   See application file for complete search history.

(56) References Cited

U.S. PATENT DOCUMENTS

| | | | |
|---|---|---|---|
| 6,013,470 A | 1/2000 | Lesage et al. | |
| 2002/0137202 A1* | 9/2002 | Burgess | |

FOREIGN PATENT DOCUMENTS

| | | | |
|---|---|---|---|
| EP | 0 799 889 A1 | 10/1997 | |
| WO | WO 99/37762 A1 | 7/1999 | |
| WO | WO 00/00610 A2 | 1/2000 | |
| WO | WO 00/27871 A2 | 5/2000 | |
| WO | WO 00/53628 A2 | 9/2000 | |
| WO | WO 01/57270 A2 | 8/2001 | |
| WO | WO 01/57272 A2 | 8/2001 | |
| WO | WO 01/57275 A2 | 8/2001 | |
| WO | WO 01/57276 A2 | 8/2001 | |
| WO | WO 01/57278 A2 | 8/2001 | |
| WO | WO 01/77174 A2 | 10/2001 | |
| WO | WO 02/26983 A2 | 4/2002 | |

OTHER PUBLICATIONS

Duprat, et al., "Task, a human a background K+ channel to sense external pH variations near physiological pH" *EMBO Journal* (1997) vol. 16, pp. 5464-5471.
Rajan, et al., "TASK-3, a Novel Tandem Pore Domain Acid-sensitive K+Channel. An Extracellular Histidine as pH Sensor" *J. of Biological Chemistry* (2000) vol. 275, pp. 16650-16657.
Spiegel, et al., "Genomic Sequence for *Homo sapiens* Clone 431C18 From Chromosome 8 (locus D8S1741), complete sequence." *Database EMBL 'Online! accession: AC007869* (1999).
Kim, Yangmi et al; *The Journal of Biological Chemistry;* Mar. 31, 2000; pp. 9340-9347; vol. 275, No. 13.

* cited by examiner

*Primary Examiner*—Michael Pak
(74) *Attorney, Agent, or Firm*—Banner & Witcoff, Ltd.

(57) ABSTRACT

The present invention provides nucleic acid and protein sequences for a novel potassium channel protein, KCNB. The herein-disclosed sequences can be used for any of a number of purposes, including for the specific detection of KCNB, for the identification of molecules that associate with and/or modulate the activity of KCNB, to diagnose any of a number of conditions associated with KCNB or KCNB activity, or to modulate the number or activity of KCNB molecules in a mammal.

15 Claims, 4 Drawing Sheets

```
KCNK3   1 mkrqnvrtlalivctftyllvgaavfdalesepelierqrlelrqqelra 50
          |||||||||.||||||||||||||||||:  |: | ::|.  :   ::
KCNB    1 MKRQNVR TLSLIVCTFTYLLVGAAVFDAL ESDHEMREEEKLKAEEIRIKG 50
                  M1

51 rynlsqggyeelervvlrlkphkagvqwrfagsfyfaitvittigyghaa 100
          :||:|   |  :||  |:|. .||:|||||:||||||||||||||||||
       51 KYNISSEDYRQLELVILQSEPHRAGVQWKFAG SFYFAITVITTIGYGHAA 100
                                          P1

101 pstdggkvfcmfyallgipltlvmfqslgerintlvryllhrakkglgmr 150
          |  || ||  ||||||.|||||||||||||.|| ||||| |  || |||
      101 PGT DAGKAFCMFYAVLGIPLTLVMFQSL GERMNTFVRYLLKRIKKCCGMR 150
              M2

151 radvsmanmvligffscistlcigaaafshyehwtffqayyycfitltti 200
          ||||  ||| :|||||. ||||||||| |  |.||  ||||||||||||
      151 NTD VSMENMVTVGFFSCMGTLCIGAAA FSQCEEWS FFHAYYYCFITLTTI 200
              M3                              P2

201 gfgdyvalqkdqalqtqpqyvafsfvyiltgltvigaflnlvvlrfmtmn 250
          ||||||||    |||  .|  ||||.||| ||||||||||||||||:|||
      201 GFGDYVALQ TKGALQKKPI YVAFSFMYILVGLTVIGAFLNLVVI RFLTMN 250
                                                         M4

251 aedekrdaehralltrngqaggggggsahttdtasstaaaggggfrnvy 300
          .|||:||||  |  |        |          |  :       .
      251 SEDERRDAEERASL......AGNRNSMVIHIPEEPRPSRP.......RYK 287

301 aevlhfqsmcsclwyksreklqysipmiiprdlstsdtcveqshsspggg 350
          |:|   ||.||| |:|.:   |   : |..  ..              ||
      288 ADVPDLQSVCSCTCYRSQD...YGGRSVAPQNSFSAKLAPHYFHSISYKI 334

351 grysdtpsrrclcsgaprsaissvstglhslstfrglmkrrssv. 394
          |  :  |   | | |||:| ||||  . ||||| ||
      351 EEISPSTLKNSL...FP.SPISSISPGLHSFTDHQRLMKRRKSV* 375
```

FIG. 1.

NUCLEIC ACID ENCODING KCNB POTASSIUM CHANNEL

CROSS-REFERENCE TO RELATED APPLICATIONS

The present application claims the benefit of priority to U.S. Provisional Application No. 60/186,915, filed Mar. 3, 2000, which is incorporated by reference herein.

BACKGROUND OF THE INVENTION

Potassium ion channels ($K^+$ channels) are ubiquitous transmembrane proteins that are major determinants of the membrane potential, i.e., the voltage difference that is present across plasma membranes, of almost all animal cells. In excitable cells, the $K^+$ channels define the frequency and duration of action potentials, and play a fundamental role in neuronal integration, muscle contraction, and hormonal secretion. In nonexcitable cells, the $K^+$ channels are pivotal to the maintenance of membrane potentials and the regulation of cell volume. These channels are thus important targets for the development of modulators that can be used to regulate fundamental cellular electrophysiology, particularly for use in therapeutic applications.

SUMMARY OF THE INVENTION

The present invention provides isolated nucleic acids encoding a novel $K^+$ channel protein, KCNB (Potassium Channel expressed in Breast). The herein-disclosed sequences can be used for any of a number of purposes, including for the specific detection of cells expressing KCNB, for the identification of molecules that associate with and/or modulate the activity of KCNB, or for the diagnosis of any of a number of conditions associated with $K^+$ channel activity or expression, for example cancer. The nucleic acid and the novel receptor it encodes are referred to herein as, inter alia, KCNB.

In one aspect, the present invention provides an isolated nucleic acid encoding a polypeptide comprising at least 70% amino acid sequence identity, often greater than 90% or 95% sequence identity, to SEQ ID NO:1. In one embodiment, the nucleic acid encodes a polypeptide that specifically binds to polyclonal antibodies generated against an amino acid sequence of SEQ ID NO:1. In another embodiment, the nucleic acid encodes a polypeptide that has a potassium channel activity. In another embodiment, the nucleic acid encodes a protein comprising an amino acid sequence of SEQ ID NO:1.

In further embodiments, the nucleic acid comprises a nucleotide sequence of SEQ ID NO:2 or SEQ ID NO:5 or can be amplified by primers that specifically hybridize under stringent conditions to a nucleic acid having a nucleotide sequence of SEQ ID NO:2 or SEQ ID NO:5.

In another aspect, the invention provides an isolated nucleic acid that specifically hybridizes under stringent hybridization conditions to a nucleic acid having a nucleotide sequence of SEQ ID NO:1.

In another aspect, the invention provides an isolated nucleic acid encoding a polypeptide comprising at least 70% amino acid identity, often greater than 90% or 95% sequence identity, to a polypeptide having an amino acid sequence of SEQ ID NO:1, wherein the nucleic acid selectively hybridizes under moderately stringent hybridization conditions to a nucleotide sequence of SEQ ID NO:1.

In another embodiment, the invention provides an isolated polypeptide comprising at least 70% amino acid sequence identity, often greater than 90% or 95% sequence identity, to an amino acid sequence of SEQ ID NO:1. In one embodiment, the polypeptide specifically binds to polyclonal antibodies generated against SEQ ID NO:1. In another embodiment the polypeptide has a potassium channel activity. In an additional embodiment, the polypeptide has an amino acid sequence of SEQ ID NO:1.

In another aspect the invention provides an antibody that selectively binds to a polypeptide that comprises at least 70% amino acid identity, often greater than 90% or 95% sequence identity, to an amino acid sequence of SEQ ID NO:1.

In another aspect, the invention provides an expression vector comprising a nucleic acid encoding a polypeptide comprising at least 70% amino acid sequence identity, often greater than 90% or 95% sequence identity, to SEQ ID NO:1. In another aspect, the invention provides a host cell transfected with the vector.

The present invention also provides a method of identifying a compound that modulates potassium channel activity, the method comprising: (i) contacting the compound with a polypeptide comprising at least 70% amino acid sequence identity, often greater than 90% or 95% sequence identity, to SEQ ID NO:1; and (ii) determining the functional effect of the compound on the polypeptide. In one embodiment, the polypeptide is linked to a solid phase, e.g. covalently linked to a solid phase.

In one embodiment, the functional effect is determined by measuring changes in ion flux. In another embodiment, the functional effect is determined by measuring binding of the compound to the polypeptide. In a further embodiment the polypeptide is recombinant. In some embodiments, the polypeptide comprises an amino acid sequence of SEQ ID NO:1 or is expressed in a cell or cell membrane. The cell can be a eukaryotic cell, e.g., a neuron.

In another aspect, the invention provides a method of identifying a modulator of KCNB activity, the method comprising: (i) contacting a KCNB with a candidate modulator; and (ii) determining whether the candidate modulator has a functional effect on the KCNB. In one embodiment, the KCNB comprises a polypeptide comprising at least 70% amino acid sequence identity, often greater than 90% or 95% sequence identity, to the amino acid sequence of SEQ ID NO:1. In another embodiment, the KCNB comprises a polypeptide having at least 30 contiguous amino acids of the amino acid sequence of SEQ ID NO:1. In a further embodiment, the KCNB comprises the amino acid sequence of SEQ ID NO:1. In further embodiments, the KCNB has potassium channel activity or is linked, e.g., covalently linked, to a solid phase.

In some embodiments, the functional effect is determined by measuring a change in ion flux or by measuring binding of the compound to the KCNB.

In another embodiment, the polypeptide is expressed in a cell or cell membrane. The cell can be a eukaryotic cell such as a neuron or a tumor cell. In one embodiment, the eukaryotic cell is a tumor cell in which KCNB is amplified in the cell or cell membrane compared to normal.

In another aspect, the invention provides a method of detecting cancer cells in a biological sample from a mammal, often a human, the method comprising steps of: (i) providing the biological sample from the mammal; and (ii) detecting a KCNB nucleic acid molecule in a sample from the mammal, wherein an increase in the KCNB nucleic acid in the sample compared to normal indicates the presence of cancer cells. In one embodiment, the KCNB nucleic acid molecule comprises greater than 70% nucleic acid sequence identity to the nucleic acid sequence of SEQ ID NO:2. In another embodiment, the KCNB nucleic acid molecule comprises at least 50 contiguous nucleotides of the nucleic acid sequence of SEQ ID NO:2 or SEQ ID NO:5. In an alternative embodiment, the nucleic acid sequence comprises the sequence of SEQ ID NO:2 or SEQ ID NO:5.

In a further embodiment, the detecting step further comprises: (a) contacting the gene with a probe that selectively hybridizes to the KCNB nucleic acid molecule under conditions in which the probe selectively hybridizes to the gene to form a stable hybridization complex; and (b) detecting the hybridization complex. In one embodiment, the contacting step further comprises a step of amplifying the KCNB nucleic acid molecule in an amplification reaction. In some embodiment, the amplification reaction is a polymerase chain reaction.

In another embodiment, the cancer cells are cells selected from the group consisting of breast cancer cells, lung cancer cells, colon cancer cells, and prostate cancer cells. Often, the cancer cells are breast cancer cells or lung cancer cells.

In another aspect, the invention provides a method of detecting cancer cells in a biological sample from a mammal, often a human, the method comprising steps of: (i) providing the biological sample from the mammal; and (ii) detecting an overexpression of a KCNB polypeptide, thereby detecting the presence of cancer cells in the biological sample. In one embodiment, the KCNB polypeptide comprises greater than 70% amino acid sequence identity, often greater than 90% or 95% sequence identity, to the nucleic acid sequence of SEQ ID NO:1. In another embodiment, the KCNB polypeptide comprises at least 50 contiguous nucleotides of the amino acid sequence of SEQ ID NO:1. In a further embodiment, the polypeptide comprises the sequence of SEQ ID NO:1.

In one embodiment, the polypeptide is detected using an antibody that selectively binds to the polypeptide. Often, the polypeptide is quantified by immunoassay.

In some embodiments, the cancer cells are cells selected from the group consisting of breast cancer cells, lung cancer cells, colon cancer cells, and prostate cancer cells. Frequently, the cancer cells are breast or lung cancer cells.

In another aspect, the invention provides a method of inhibiting proliferation of a cancer cell that overexpresses a KCNB polypeptide comprising at least 70% amino acid identity, often greater than 90% or 95% sequence identity, to SEQ ID NO:1, the method comprising the step of contacting the cancer cell with a therapeutically effective amount of an inhibitor of the KCNB polypeptide. In some embodiments, the cancer cell is selected from the group consisting of a breast, lung, colon, or prostate cancer cell. Often the cancer cell is a breast cancer cell or lung cancer cell. In one embodiment, the KCNB polypeptide has an amino acid sequence of SEQ ID NO:1. In other embodiments, the inhibitor is an antibody or an antisense polynucleotide.

In another aspect the invention provides a method of treating a KCNB-associated disorder, the method comprising administering a therapeutically effective amount of a modulator of KCNB.

In aspect, the invention provides a method of treating a disease or condition associated with a potassium channel protein, the method comprising administering to a patient an antibody that selectively binds to an isolated potassium channel polypeptide comprising greater than 70% amino acid identity, often greater than 90% or 95% sequence identity, to SEQ ID NO:1. In one embodiment aspect, the present invention provides an isolated nucleic acid encoding a polypeptide, wherein the nucleic acid specifically hybridizes under stringent hybridization conditions to a nucleic acid comprising a nucleotide sequence of SEQ ID NO:2 or SEQ ID NO:5.

BRIEF DESCRIPTION OF THE DRAWINGS

FIG. 1 illustrates the amino acid sequences corresponding to the domains of KCNB (SEQ ID NO:1). The homology to the amino acid sequence of KCNK3 (SEQ ID NO:15) is also shown.

DETAILED DESCRIPTION OF THE INVENTION AND PREFERRED EMBODIMENTS

I. Introduction

Figure 2:
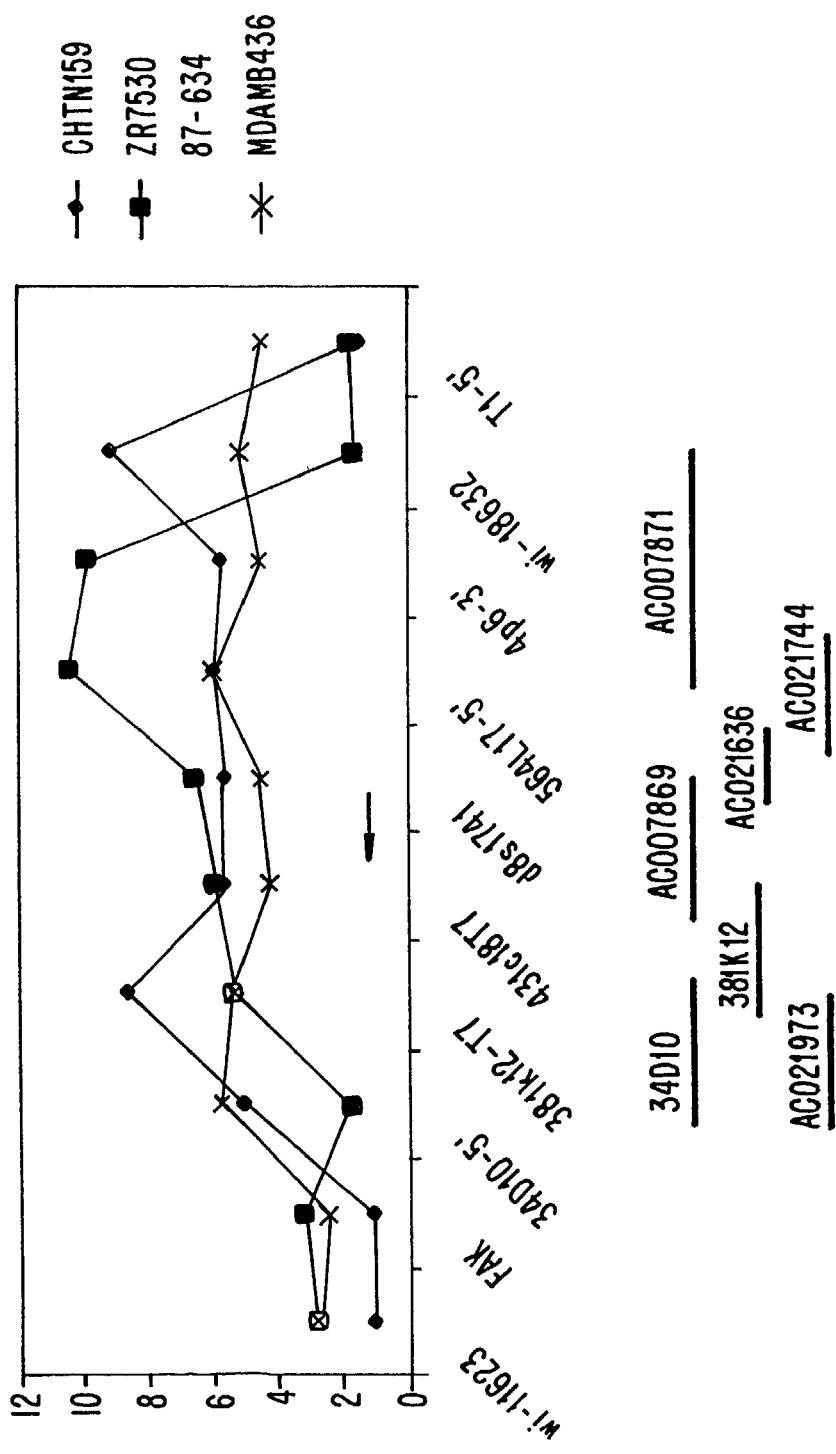
FIG. 2 is a schematic drawing of the genomic DNA amplification epicenter and physical map at the KCNB locus. The x-axis shows 10 markers in a region of human chromosome 8q24.3. The y-axis represents the DNA copy number for each marker defined in the x-axis. The KCNB gene is indicated by an arrow. The human genomic DNA clones are not the scale of the actual clone sizes. The 10 markers are placed at equal intervals, not to the scale of actual distance, for viewing purposes.

The present invention provides for isolated nucleic acid and amino acid sequences encoding KCNB and methods of production of KCNB. Tissues or cell types that express KCNB include, but are not limited to, brain, pancreas, kidney, breast, lung colon, spleen, liver, placenta, stomach, ovary, prostate, bladder and peripheral blood monocye cells. Structurally, the full length nucleotide sequence of KCNB (SEQ ID NO:2 and SEQ ID NO:5) encodes a polypeptide of 374 amino acids in length (SEQ ID NO:1). The amino acid sequence can be aligned with a 62% sequence identity with the amino acid sequence of the potassium channel protein KCNK3, or TASK, which is a member of the TWIK-1 family of potassium channels (see, e.g., Duprat et al., *EMBO J.* 16:5464-5471, 1997; U.S. Pat. No. 6,013,470; and WO99/37762) defined by the presence of 2 pore (P) domains and 4 transmembrane-spanning regions. The conservation of the 2 pore domains and 4 transmembrane domains of the TWIK family of K$^+$ channels is not necessarily associated with a conservation of functional properties: a TWIK family member has been identified that gives rise to weakly inward rectifier K$^+$ currents; another produces outward rectifier K$^+$ currents. Both channels are open at the resting potential and are able to drive the resting membrane potential near the K$^+$ equilibrium potential. KCNK3 (or TASK) produces K$^+$ currents that possess the characteristic of background conductances and is very sensitive to variation of extracellular pH in a narrow physiological range (see, e.g., Duprat et al., supra). Unlike KCNB, TASK has not been observed to be overexpressed in cancer.

The invention also provides methods of screening for modulators, e.g., activators, inhibitors, stimulators, enhancers, etc., of KCNB nucleic acids and proteins. Such modulators can affect KCNB activity, e.g., by modulating KCNB transcription, translation, mRNA or protein stability; by altering the interaction of KCNB with the plasma membrane, or other molecules; or by affecting KCNB protein activity. In one embodiment, compounds are screened, e.g., using high throughput screening (HTS), to identify those compounds that can bind to and/or modulate the activity of an isolated KCNB polypeptide or fragment thereof. In another embodiment, KCNB proteins are recombinantly expressed in cells, and the modulation of KCNB is assayed by using any measure of potassium ion channel function, such as measurement of the membrane potential. Methods to measure the membrane potential include, for example, patch clamp techniques, measurement of whole cell currents, radiolabeled rubidium flux assays, and fluorescence assays using voltage-sensitive dyes.

In numerous embodiments, a KCNB polynucleotide or polypeptide is introduced into a cell, in vivo or ex vivo, and the KCNB activity in the cell is thereby modulated. For example, a polynucleotide encoding a full length KCNB polypeptide can be introduced into a population of cells, thereby modulating the electrophysiological properties of the cells.

In certain embodiments, monoclonal or polyclonal antibodies directed to KCNB, preferably an N-terminal domain, C-terminal domain, transmembrane domain, or extracellular loop of KCNB, will be administered to a mammal to inhibit the activity of KCNB in cells. Such embodiments are useful, e.g., in the treatment of a disease or disorder associated with KCNB activity, e.g., cancer.

The present invention also provides methods for detecting KCNB nucleic acid and protein expression. KCNB polypeptides can also be used to generate monoclonal and polyclonal antibodies useful for the detection of KCNB-expressing cells or for the amelioration of KCNB activity. Cells that express KCNB can also be identified using techniques such as reverse transcription and amplification of mRNA, isolation of total RNA or poly A+RNA, northern blotting, dot blotting, in situ hybridization, RNase protection, SI digestion, probing DNA microchip arrays, western blots, and the like.

Functionally, KCNB nucleic acids encode a potassium ion channel protein. Specific regions of the KCNB nucleotide and amino acid sequences may be used to identify polymorphic variants, interspecies homologs, and alleles of KCNB genes. Identification can be performed by using in vitro techniques, e.g., by using PCR under stringent or moderate hybridization conditions, or by using the sequence information in a computer system for comparison with other nucleotide sequences. Sequence comparison can be performed using any of the sequence comparison algorithms discussed herein below. Antibodies that bind specifically to KCNB polypeptides or a conserved region thereof, e.g., the C-terminal region of KCNB, can also be used to identify alleles, interspecies homologs, and polymorphic variants.

Polymorphic variants, interspecies homologs, and alleles of KCNB are typically confirmed by comparing a KCNB polypeptide having an amino acid sequence of SEQ ID NO:1 to the putative KCNB protein to demonstrate the identification of a polymorphic variant or allele of the KCNB gene or protein. Such variants or homologs can be confirmed as having the same functional characteristics by expressing the variant and analyzing the activity, e.g., by determining the electrophysiological properties as described herein.

Nucleotide and amino acid sequence information for KCNB are also used to construct models of KCNB proteins. These models are subsequently used to identify compounds that can activate or inhibit KCNB proteins. Such compounds that modulate the activity of KCNB genes or proteins can be used to investigate the physiological role of KCNB genes.

The present invention also provides assays, preferably high throughput screening (HTS) assays, to identify compounds or other molecules that interact with and/or modulate KCNB. In certain assays, a particular domain of KCNB is used, e.g., an N-terminal, transmembrane, pore or C-terminal domain may be used.

The present invention also provides methods to treat diseases or conditions associated with KCNB activity. For example, the present methods can be used to diagnose, determine the prognosis for, or treat, any of a number of types of cancers. In preferred embodiments, the cancer is an epithelial cancer, e.g., breast, lung, prostate, kidney, stomach, bladder, or ovarian cancer, or any cancer of the gastrointestinal tract.

The diagnostic methods of this invention can be used in animals including, for example, primates, canines, felines, murines, bovines, equines, ovines, porcines, lagomorphs, etc, as well as in humans.

Kits are also provided for carrying out the herein-disclosed diagnostic and therapeutic methods.

II. Definitions

As used herein, the following terms have the meanings ascribed to them unless specified otherwise.

The term "KCNB" therefore refers to KCNB nucleic acid and polypeptide polymorphic variants, alleles, mutants, and interspecies homologs that: (1) have an amino acid sequence that has greater than about 65% amino acid sequence identity, 70%, 75%, 80%, 85%, 90%, preferably 91%, 92%, 93%, 94%, 95%, 96%, 97%, 98% or 99% or greater amino acid sequence identity, preferably over a region of over a region of at least about 50, 100, 200, 500, 1000, or more amino acids, to a KCNB sequence of SEQ ID NO:1; (2) bind to antibodies, e.g., polyclonal antibodies, raised against an immunogen comprising an amino acid sequence of SEQ ID NO:1, and conservatively modified variants thereof; (3) specifically hybridize under stringent hybridization conditions to a KCNB nucleic acid sequence of SEQ ID NO:2 or SEQ ID NO:5 and conservatively modified variants thereof; (4) have a nucleic acid sequence that has greater than about 95%, preferably greater than about 96%, 97%, 98%, 99%, or higher nucleotide sequence identity, preferably over a region of at least about 50, 100, 200, 500, 1000, or more nucleotides, to SEQ ID NO:2 or SEQ ID NO:5; or (5) are amplified by primers that specifically hybridize under stringent hybridization conditions to the same sequence as a primer set selected from the group consisting of SEQ ID NOs: 3 and 4; SEQ ID NOs: 6 and 7, and SEQ ID NOs: 9 and 10. A KCNB polynucleotide or polypeptide sequence is typically from a mammal including, but not limited to, human, rat, mouse, hamster, cow, pig, horse, sheep, or any mammal. A "KCNB polynucleotide" and a "KCNB polypeptide," are both either naturally occurring or recombinant. The human KCNB gene is located at chromosome 8q24.3.

A "full length" KCNB protein or nucleic acid refers to a KCNB polypeptide or polynucleotide sequence, or a variant thereof, that contains all of the elements normally contained in one or more naturally occurring, wild type KCNB polynucleotide or polypeptide sequences. It will be recognized, however, that derivatives, homologs, and fragments of KCNB can be readily used in the present invention. Such KCNB variants can comprise any one or more of the domains of the polypeptide shown as SEQ ID NO:1, or multiple copies of any one or more domains, or any number of domains in novel combinations with each other or with other proteins or protein domains.

Topologically, full-length KCNB polypeptides as defined herein are considered to have an amino terminal domain, two pore domains, four transmembrane domains, and a C-terminal domain (FIG. 1). These domains can be structurally identified using methods known to those of skill in the art, such as sequence analysis programs that identify hydrophobic and hydrophilic domains (see, e.g., Stryer, *Biochemistry* (3rd ed. 1988); see also any of a number of Internet based sequence analysis programs, such as those found at dot.imgen.bcm.t-mc.edu).

The "C-terminal domain", which, e.g., corresponds to the amino acids of from about 250 to about 374 of SEQ ID NO:1, refers to the region of the protein that extends from about the fourth transmembrane domain to the C-terminus of the protein. This domain is a hallmark of KCNB and its homologs, and has less than about 30%, optionally less than about 50%, 40%, or 35%, sequence identity with KCNK3.

"P domain" refers to a structural region of the protein the encodes a pore domain, which is a characteristic feature of potassium ion channels (see, e.g., Heginbotham et al., *Biophys. J.* 66:1061-1067, 1994). KCNB has two pore domains, i.e., two P domains.

"Transmembrane domain" refers to a hydrophobic protein domain that lies within and spans the plasma membrane, and may also include the corresponding cytoplasmic (intracellular) and extracellular loops. The transmembrane domains of KCNB can be identified using standard methods, as described in Kyte & Doolittle, *J. Mol. Biol.* 157:105-132 (1982)), or in Stryer, supra. KCNB has four transmembrane domains.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given polypeptide. For instance, the codons CGU, CGC, CGA, CGG, AGA, and AGG all encode the amino acid arginine. Thus, at every position where an arginine is specified by a codon, the codon can be altered to any of the corresponding codons described without altering the encoded polypeptide. Such nucleic acid variations are "silent substitutions" or "silent variations," which are one species of "conservatively modified variations." Every polynucleotide sequence described herein which encodes a polypeptide also describes every possible silent variation, except where otherwise noted. Thus, silent substitutions are an implied feature of every nucleic acid sequence which encodes an amino acid. One of skill will recognize that each codon in a nucleic acid (except AUG, which is ordinarily the only codon for methionine) can be modified to yield a functionally identical molecule by standard techniques. In some embodiments, the nucleotide sequences that encode the enzymes are preferably optimized for expression in a particular host cell (e.g., yeast, mammalian, plant, fungal, and the like) used to produce the enzymes.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:

1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M)
(see, e.g., Creighton, Proteins (1984)).

Macromolecular structures such as polypeptide structures can be described in terms of various levels of organization. For a general discussion of this organization, see, e.g., Alberts et al., *Molecular Biology of the Cell* (3rd ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains. Domains are portions of a polypeptide that form a compact unit of the polypeptide and are typically 50 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A "cancer" in an animal refers to the presence of cells possessing characteristics typical of cancer-causing cells, such as uncontrolled proliferation, immortality, metastatic potential, rapid growth and proliferation rate, and certain characteristic morphological features and cellular markers. In some circumstances, cancer cells will be in the form of a tumor, but such cells may exist alone within an animal, or may circulate in the blood stream as independent cells, such as leukemic cells.

"Biological sample," as used herein, refers to a sample of biological tissue or fluid that contains one or more KCNB nucleic acids encoding one or more KCNB proteins. Such samples include, but are not limited to, tissue isolated from humans, mice, and rats, in particular, breast and lung tissue as well as blood, lymphatic tissue, liver, brain, heart, spleen, testis, ovary, thymus, kidney, and embryonic tissues. Biological samples may also include sections of tissues such as frozen sections taken for histological purposes. A biological sample is typically obtained from a eukaryotic organism, such as insects, protozoa, birds, fish, reptiles, and preferably a mammal such as rat, mouse, cow, dog, guinea pig, or rabbit, and most preferably a primate such as a chimpanzee or a human.

By "determining the functional effect" is meant assaying the effect of a compound that increases or decreases a parameter that is indirectly or directly under the influence of a KCNB polypeptide e.g., functional, physical and chemical effects. Such functional effects include, but are not limited to, changes in ion flux, membrane potential, current amplitude, voltage gating, and pH sensitivity as well as other biological effects such as changes in gene expression of KCNB or of any marker genes, and the like. The ion flux can include any ion that passes through the channel, e.g., potassium or rubidium, and analogs thereof such as radioisotopes. Such functional effects can be measured by any means known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties,.

"Inhibitors," "activators," and "modulators" of KCNB genes or proteins are used interchangeably to refer to inhibitory, activating, or modulating molecules identified using in vitro and in vivo assays for KCNB activity or number. Such modulating molecules, also referred to herein as compounds, include polypeptides, antibodies, amino acids, nucleotides, lipids, carbohydrates, or any organic or inorganic molecule. Inhibitors are compounds that, e.g., delay, or partially or totally block KCNB activity, desensitize KCNB, or downregulate KCNB expression or stability. Activators are compounds that, e.g., open KCNB channels, sensitize KCNB or stimulate KCNB activity, or increase KCNB expression or stability Assays for inhibitors and activators are described below and include, e.g., expressing KCNB proteins in cells or cell membranes, applying putative modulators, and then determining the functional effects on the electrophysiological properties of the cells. Measures of functional effects include, e.g., determining changes in the membrane potential. Methods for measuring membrane potential include, but are not limited to, patch clamp techniques, determination of whole cell currents, radiolabeled rubidium flux assays and fluorescence assays using voltage-sensitive dyes.

Samples or assays comprising KCNB polypeptides that are treated with a potential activator, inhibitor, or modulator are compared to control samples without the inhibitor, activator, or modulator to examine the effect of the candidate compound. Control samples (untreated with the compound) are assigned a relative KCNB activity value of 100%. Inibition of a KCNB polypeptide is achieved when the activity value relative to the control is about 80%, optionally about 50% or 25-0%. Activation of a KCNB polypeptide is achieved when the activity value relative to the control is about 110%, optionally about 150%, optionally about 200-500%, or about 1000-3000% higher.

The terms "isolated", "purified", or "biologically pure" refer to material that is substantially or essentially free from components which normally accompany it as found in its native state. Purity and homogeneity are typically determined using analytical chemistry techniques such as polyacrylamide gel electrophoresis or high performance liquid chromatography. A protein that is the predominant species present in a preparation is substantially purified. In particular, an isolated KCNB nucleic acid is separated from open reading frames that flank the KCNB gene and encode proteins other than KCNB. The term "purified" denotes that a nucleic acid or protein gives rise to essentially one band in an electrophoretic gel. Particularly, it means that the nucleic acid or protein is at least 85% pure, optionally at least 95% pure, and optionally at least 99% pure.

"Nucleic acid" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that function in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

A "label" or a "detectable moiety" is a composition detectable by spectroscopic, photochemical, biochemical, immunochemical, or chemical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

A "labeled nucleic acid probe or oligonucleotide" is one that is bound, either covalently, through a linker or a chemical bond, or noncovalently, through ionic, van der Waals, electrostatic, or hydrogen bonds to a label such that the presence of the probe may be detected by detecting the presence of the label bound to the probe.

As used herein a "nucleic acid probe or oligonucleotide" is defined as a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. The probes are optionally directly labeled as with isotopes, chromophores, lumiphores, chromogens, or indirectly labeled such as with biotin to which a streptavidin complex may later bind. By assaying for the presence or absence of the probe, one can detect the presence or absence of the select sequence or subsequence.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (nonrecombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation. The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. Typically, the expression vector includes a nucleic acid to be transcribed operably linked to a promoter.

The terms "identical" or percent "identity," in the context of two or more nucleic acids or polypeptide sequences, refer to two or more sequences or subsequences that are the same or have a specified percentage of amino acid residues or nucleotides that are the same (i.e., about 70% identity, preferably 75%, 80%, 85%, 90%, 91%, 92%, 93%, 94%, 95%, 96%, 97%, 98%, 99%, or higher identity over a specified region (e.g., SEQ ID NOS: 1, 2, or 5), when compared and aligned for maximum correspondence over a comparison window or designated region) as measured using a BLAST or BLAST 2.0 sequence comparison algorithms with default parameters described below, or by manual alignment and visual inspection. Such sequences are then said to be "substantially identical." This definition also refers to the compliment of a test sequence. The definition also includes sequences that have deletions and/or additions, as well as those that have substitutions. As described below, the preferred algorithms can account for gaps and the like. Preferably, the identity exists over a region that is at least about 25 amino acids or nucleotides in length, or more preferably over a region that is 50, 60, 70, 80, 90, or 100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Another example of algorithm that is suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, *Proc. Natl. Acad. Sci. USA* 89:10915 (1989)) alignments (B) of 50, expectation (E) of 10, M=5, N=−4, and a comparison of both strands.

The BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively (or specifically) hybridizes to" refers to the binding, duplexing, or hybridizing of a molecule only to a particular nucleotide sequence under stringent hybridization conditions when that sequence is present in a complex mixture (e.g., total cellular or library DNA or RNA).

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C for short probes (e.g., 10 to 50 nucleotides) and at least about 600 C for long probes (e.g., greater than 50 nucleotides). Stringent conditions may also be achieved with the addition of destabilizing agents such as formamide. For selective or specific hybridization, a positive signal is at least two times background, optionally 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C. Such washes can be performed for 5, 15, 30, 60, 120, or more minutes. For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. Such washes can be performed for 5, 15, 30, 60, 120, or more minutes. A positive hybridization is at least twice background. Those of ordinary skill will readily recognize that alternative hybridization and wash conditions can be utilized to provide conditions of similar stringency.

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

An exemplary immunoglobulin (antibody) structural unit comprises a tetramer. Each tetramer is composed of two identical pairs of polypeptide chains, each pair having one "light" (about 25 kDa) and one "heavy" chain (about 50-70 kDa). The N-terminus of each chain defines a variable region of about 1 00 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$—$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990)).

For preparation of monoclonal or polyclonal antibodies, any technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy* (1985)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al., *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

An "anti-KCNB" antibody is an antibody or antibody fragment that specifically binds a polypeptide encoded by a KCNB gene, cDNA, or a subsequence thereof, e.g., the C-terminal domain.

The term "immunoassay" is an assay that uses an antibody to specifically bind an antigen. The immunoassay is characterized by the use of specific binding properties of a particular antibody to isolate, target, and/or quantify the antigen.

The phrase "specifically (or selectively) binds" to an antibody or "specifically (or selectively) immunoreactive with," when referring to a protein or peptide, refers to a binding reaction that is determinative of the presence of the protein in a heterogeneous population of proteins and other biologics. Thus, under designated immunoassay conditions, the specified antibodies bind to a particular protein at least two times the background and do not substantially bind in a significant amount to other proteins present in the sample. Specific binding to an antibody under such conditions may require an antibody that is selected for its specificity for a particular protein. For example, polyclonal antibodies raised to a KCNB polypeptide from specific species such as rat, mouse, or human can be selected to obtain only those polyclonal antibodies that are specifically immunoreactive with the KCNB protein and not with other proteins, except for polymorphic variants and alleles of the KCNB protein. This selection may be achieved by subtracting out antibodies that cross-react with KCNB molecules from other species. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

The phrase "selectively associates with" refers to the ability of a nucleic acid to "selectively hybridize" with another as defined above, or the ability of an antibody to "selectively (or specifically) bind" to a protein, as defined above.

By "host cell" is meant a cell that contains an expression vector and supports the replication or expression of the expression vector. Host cells may be prokaryotic cells such as *E. coli*, or eukaryotic cells such as yeast, insect, amphibian, or mammalian cells such as CHO, HeLa and the like, e.g., cultured cells, explants, and cells in vivo. The phrase "detecting a cancer" or "diagnosing a cancer" refers to determining the presence or absence of cancer or a precancerous condition in an animal. "Detecting a cancer" can also refer to obtaining indirect evidence regarding the likelihood of the presence of cancerous cells in the animal. Detecting a cancer can be accomplished using the methods of this invention alone, in combination with other methods, or in light of other information regarding the state of health of the animal.

III. Manipulation and Detection of KCNB Nucleic Acids

In numerous embodiments of the present invention, nucleic acids encoding a KCNB polypeptide, including a full-length KCNB protein, or any derivative, variant, homolog, or fragment thereof, will be used. Such nucleic acids are useful for any of a number of applications, including for the production of KCNB protein, for diagnostic assays, for therapeutic applications, for KCNB-specific probes, for assays for KCNB binding and/or modulating compounds, to identify and/or isolate KCNB homologs from other species or from mice, and other applications.

A. General Recombinant DNA Methods

Numerous applications of the present invention involve the cloning, synthesis, maintenance, mutagenesis, and other manipulations of nucleic acid sequences that can be performed using routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

For nucleic acids, sizes are given in either kilobases (kb) or base pairs (bp). These are estimates derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides that are not commercially available can be chemically synthesized according to the solid phase phosphoramidite triester method first described by Beaucage & Caruthers, *Tetrahedron Letts.* 22:1859-1862 (1981), using an automated synthesizer, as described in Van Devanter et al., *Nucleic Acids Res.* 12:6159-6168 (1984). Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., Gene 16:21-26 (1981).

B. Isolating and Detecting KCNB Nucleotide Sequences

In numerous embodiments of the present invention, KCNB nucleic acids will be isolated and cloned using recombinant methods. Such embodiments are used, e.g., to isolate KCNB polynucleotides for protein expression or during the generation of variants, derivatives, expression cassettes, or other sequences derived from KCNB, to monitor KCNB gene expression, for the determination of KCNB sequences in various species, for diagnostic purposes in a patient, i.e., to detect mutations in KCNB, or for genotyping and/or forensic applications.

Often, the nucleic acid sequences encoding KCNB proteins and related nucleic acid sequence homologs are cloned from cDNA and genomic DNA libraries by hybridization with probes, or isolated using amplification techniques with oligonucleotide primers. For example, KCNB sequences are typically isolated from mammalian nucleic acid (genomic or cDNA) libraries by hybridizing with a nucleic acid probe, the sequence of which can be derived from SEQ ID NO:2, or amplified using primers comprising, e.g., SEQ ID NOs: 3 and 4, or 6 and 7, or 9 and 10. A suitable biological material from which RNA and cDNA for KCNB can be isolated includes such tissues as breast and lung as well as blood, lymph, brain, liver, heart, spleen, testis, ovary, thymus, kidney, embryonic, or other tissues.

Amplification techniques using primers can also be used to amplify and isolate KCNB sequences from DNA or RNA (see, e.g., Dieffenfach & Dveksler, *PCR Primer: A Laboratory Manual* (1995)). Primers can be used, e.g., to amplify either the full length sequence or a probe of from one to several hundred nucleotides (using, e.g., primers shown as SEQ ID NOs: 3 and 4), which is then used to screen a mammalian library for full-length KCNB clones.

Nucleic acids encoding KCNB polypeptides can also be isolated from expression libraries using antibodies as probes. Such polyclonal or monoclonal antibodies can be raised using the sequence of SEQ ID NO:1, or derivatives or fragments thereof.

Polymorphic variants, alleles, and interspecies homologs that are substantially identical to a KCNB gene can be isolated using KCNB nucleic acid probes, and oligonucleotides by screening libraries under stringent hybridization conditions. Alternatively, expression libraries can be used to clone KCNB polymorphic variants, alleles, and interspecies homologs, by detecting expressed homologs immunologically with antisera or purified antibodies made against a KCNB polypeptide, which also recognize and selectively bind to the KCNB homolog.

More distantly related KCNB homologs can be identified using any of a number of well known techniques, including by hybridizing a KCNB probe with a genomic or cDNA library using moderately stringent conditions, or under low stringency conditions using probes from regions which are selective for KCNB, e.g., specific probes generated to the C-terminal domain. Also, a distant homolog can be amplified from a nucleic acid library using degenerate primer sets, i.e., primers that incorporate all possible codons encoding a given amino acid sequence, in particular based on a highly conserved amino acid stretch. Such primers are well known to those of skill, and numerous programs are available, e.g., on the internet, for degenerate primer design.

To make a cDNA library, one should choose a source that is rich in KCNB mRNA, e.g., cells isolated from the brain, or breast or lung cancer cells. The mRNA is then made into cDNA using reverse transcriptase, ligated into a recombinant vector, and transfected into a recombinant host for propagation, screening and cloning. Methods for making and cloning cDNA libraries are well known (see, e.g., Gubler & Hoffman, *Gene* 25:263-269 (1983); Sambrook et al., supra; Ausubel et al., supra).

For a genomic library, the DNA is extracted from the tissue or cells and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.*, 72:3961-3965 (1975).

An alternative method of isolating KCNB nucleic acid and its homologs combines the use of synthetic oligonucleotide primers and amplification of an RNA or DNA template (see, U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of KCNB genes directly from mRNA, from cDNA, from genomic libraries or cDNA libraries. Degenerate oligonucleotides can be designed to amplify KCNB homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of KCNB-encoding mRNA in physiological samples, for nucleic acid sequencing, or for other purposes. Genes amplified by the PCR reaction can be purified from agarose gels and cloned into an appropriate vector.

Synthetic oligonucleotides can be used to construct recombinant KCNB genes for use as probes or for expression of protein. This method is performed using a series of overlapping oligonucleotides usually 40-120 bp in length, representing both the sense and non-sense strands of the gene. These DNA fragments are then annealed, ligated and cloned. Alternatively, amplification techniques can be used with precise primers to amplify a specific subsequence of the KCNB nucleic acid. The specific subsequence is then ligated into an expression vector.

The nucleic acid encoding a KCNB polypeptide is typically cloned into intermediate vectors before transformation into prokaryotic or eukaryotic cells for replication and/or expression. These intermediate vectors are typically prokaryote vectors, e.g., plasmids, or shuttle vectors. Vectors, cells, and transfection methods are well known to those of skill and are described, e.g., in Ausubel or in Sambrook, both supra.

Potassium channel activity of a polypeptide encoded by a KCNB nucleic acid can be assessed using a variety of assays known to those skilled in the art, e.g., patch clamping, using voltage-sensitive dyes, or by measuring changes in parameters such as spectroscopic characteristics (e.g., fluorescence, absorbance, refractive index), hydrodynamic (e.g., shape), chromatographic, or solubility properties. Often, the KCNB activity is assessed by using an expression assay system in which an expression vector that encodes the KCNB is transfected into a cell. The electrophysiological properties fo the cell can then be assessed compared to control cells. For example, a KCNB expression vector can be co-transfected with a plasmid, such as a green fluorescent protein-expressing plasmid, that allows identification of the transfected cells. Cellular electrophysiology can then be measured in those transfectants that express KCNB compared to transfectants that were co-transfected with the expression vector lacking the KCNB insert and the identifier plasmid. The activity of the expressed KCNB protein can be assayed using a variety of assays to measure changes in ion fluxes including patch clamp techniques, measurement of whole cell currents, radiolabeled rubidium flux assays, and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Hoevinsky et al., *J. Membrane Biol.* 137:59-70 (1994)).

Optionally, nucleic acids will be used that encode chimeric proteins comprising a KCNB polypeptide or domains thereof in combination with a heterologous polypeptide or polypeptides. For example, a domain such as an N-terminal or C-terminal domain, an extracellular loop, or a transmembrane domain of KCNB can be covalently linked to a heterologous protein such as a heterologous transmembrane domain or a heterologous extracellular domain. Other heterologous proteins of choice include, e.g., luciferase, GFP, and β-gal.

In certain embodiments, KCNB polynucleotides will be detected using hybridization-based methods to determine, e.g., KCNB RNA levels or to detect particular DNA sequences, e.g., for diagnostic or prognostic applications. A KCNB polynucleotide level can be detected by detecting any KCNB DNA or RNA, including genomic DNA, mRNA, and cDNA. Detection can involve quantification of the level of polynucleotide (e.g., genomic DNA, cDNA, or mRNA), or, alternatively, can be a qualitative assessment of the level, or of the presence or absence, of KCNB, in particular in comparison with a control level. Any of a number of methods to detect any of the above can be used, as described infra. Such methods include, for example, hybridization, amplification, and other assays.

In certain embodiments, the ability to detect an increased level, or diagnostic presence, in a cell is used as a marker for cancer cells, i.e., to monitor the number or localization of cancer cells in a patient, as detected in vivo or in vitro.

Gene expression of KCNB can be analyzed by techniques known in the art, e.g., Northern blotting, reverse transcription and PCR amplification of mRNA, including quantitative PCR analysis of mRNA levels with real-time PCR procedures (e.g., reverse transcriptase-TAQMAN™ amplification), dot blotting, in situ hybridization, RNase protection, probing DNA microchip arrays, and the like. In one embodiment, high density oligonucleotide analysis technology (e.g., GeneChip™) is used to identify homologs and polymorphic variants of KCNB, or to monitor levels of KCNB mRNA. In the case where KCNB is linked to a known disease, e.g., cancer, they can be used with GeneChip™ as a diagnostic tool in detecting the disease in a biological sample, see, e.g., Gunthand et al., *AIDS Res. Hum. Retroviruses* 14: 869-876 (1998); Kozal et al., *Nat. Med.* 2:753-759 (1996); Matson et al., *Anal. Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998).

In one embodiment, e.g., for the diagnosis of cancer, the copy number, i.e., the number of KCNB genes in a cell, is evaluated. Generally, for a given autosomal gene, an animal has two copies of each gene. The copy number can be increased, however, by gene amplification or duplication, e.g., in cancer cells, or reduced by deletion. Methods of evaluating the copy number of a particular gene are well known to those of skill in the art, and include, inter alia, hybridization and amplification based assays.

Any of a number of hybridization based assays can be used to detect the KCNB gene or the copy number in the cells of a biological sample. One such method is by Southern blot. In a Southern blot, genomic DNA is typically fragmented, separated electrophoretically, transferred to a membrane, and subsequently hybridized to a KCNB-specific probe. For copy number determination, comparison of the intensity of the hybridization signal from the probe for the target region with a signal from a control probe for a region of normal genomic DNA (e.g., a nonamplified portion of the same or related cell, tissue, organ, etc.) provides an estimate of the relative KCNB copy number. Southern blot methodology is well known in the art and is described, e.g., in Ausubel et al., or Sambrook et al., supra.

An alternative means for determining the copy number of KCNB genes in a sample is by in situ hybridization, e.g., fluorescence in situ hybridization, or FISH. In situ hybridization assays are well known (e.g., Angerer (1987) *Meth. Enzymol* 152: 649). Generally, in situ hybridization comprises the following major steps: (1) fixation of tissue or biological structure to be analyzed; (2) prehybridization treatment of the biological structure to increase accessibility of target DNA, and to reduce nonspecific binding; (3) hybridization of the mixture of nucleic acids to the nucleic acid in the biological structure or tissue; (4) post-hybridization washes to remove nucleic acid fragments not bound in the hybridization and (5) detection of the hybridized nucleic acid fragments.

The probes used in such applications are typically labeled, e.g., with radioisotopes or fluorescent reporters. Preferred probes are sufficiently long, e.g., from about 50, 100, or 200 nucleotides to about 1000 or more nucleotides, so as to specifically hybridize with the target nucleic acid(s) under stringent conditions.

In numerous embodiments, "comparative probe" methods, such as comparative genomic hybridization (CGH), are used to detect gene amplification. In comparative genomic hybridization methods, a "test" collection of nucleic acids is labeled with a first label, while a second collection (e.g., from a healthy cell or tissue) is labeled with a second label. The ratio of hybridization of the nucleic acids is determined by the ratio of the first and second labels binding to each fiber in an array. Differences in the ratio of the signals from the two labels, e.g., due to gene amplification in the test collection, is detected and the ratio provides a measure of the KCNB gene copy number.

Hybridization protocols suitable for use with the methods of the invention are described, e.g., in Albertson (1984) *EMBO J.* 3: 1227-1234; Pinkel (1988) *Proc. Natl. Acad. Sci. USA* 85: 9138-9142; EPO Pub. No. 430,402; *Methods in Molecular Biology, Vol. 33: In Situ Hybridization Protocols*, Choo, ed., Humana Press, Totowa, N.J. (1994), etc.

In another embodiment, amplification-based assays are used to detect KCNB expression or to measure the copy number of KCNB genes. In such assays, the KCNB nucleotide sequences present in a sample serve as a template in an amplification reaction (e.g., PCR). In a quantitative amplification, the amount of amplification product will be proportional to the amount of template in the original sample. Comparison to appropriate controls provides a measure of the level of KCNB polynucleotide in the sample. Methods of quantitative amplification are well known to those of skill in the art. Detailed protocols for quantitative PCR are provided, e.g., in Innis et al. (1990) *PCR Protocols, A Guide to Methods and Applications*, Academic Press, Inc. N.Y.). The nucleic acid sequence for KCNB (see, e.g., SEQ ID NO:2 or SEQ ID NO:5) is sufficient to enable one of skill to routinely select primers to amplify any portion of the gene.

In some embodiments, a TaqMan based assay is used to quantify KCNB polynucleotides. TaqMan based assays use a fluorogenic oligonucleotide probe that contains a 5' fluorescent dye and a 3' quenching agent. The probe hybridizes to a PCR product, but cannot itself be extended due to a blocking agent at the 3' end. When the PCR product is amplified in subsequent cycles, the 5' nuclease activity of the polymerase, e.g., AmpliTaq, results in the cleavage of the TaqMan probe. This cleavage separates the 5' fluorescent dye and the 3' quenching agent, thereby resulting in an increase in fluorescence as a function of amplification (see, for example, literature provided by Perkin-Elmer, e.g., www2.perkin-elmer.com).

Other suitable amplification methods include, but are not limited to, ligase chain reaction (LCR) (see, Wu and Wallace (1989) *Genomics* 4: 560, Landegren et al. (1988) Science 241: 1077, and Barringer et al. (1990) *Gene* 89: 117), transcription amplification (Kwoh et al. (1989) *Proc. Natl. Acad. Sci. USA* 86: 1173), self-sustained sequence replication (Guatelli et al. (1990) *Proc. Nat. Acad. Sci. USA* 87: 1874), dot PCR, and linker adapter PCR, etc.

C. Expression in Prokaryotes and Eukaryotes

To obtain high level expression of a cloned gene or nucleic acid, such as a cDNA encoding a KCNB polypeptide, a KCNB sequence is typically subcloned into an expression vector that contains a strong promoter to direct transcription, a transcription/translation terminator, and if for a nucleic acid encoding a protein, a ribosome binding site for translational initiation. Suitable bacterial promoters are well known in the art and are described, e.g., in Sambrook et al. and Ausubel et al. Bacterial expression systems for expressing the KCNB protein are available in, e.g., *E. coli*, Bacillus sp., and Salmonella (Palva et al., Gene 22:229-235 (1983); Mosbach et al., Nature 302:543-545 (1983). Kits for such expression systems are commercially available. Eukaryotic expression systems for mammalian cells, yeast, and insect cells are well known in the art and are also commercially available. In one embodiment, the eukaryotic expression vector is an adenoviral vector, an adeno-associated vector, or a retroviral vector.

For therapeutic applications, KCNB nucleic acids are introduced into a cell, in vitro, in vivo, or ex vivo, using any of a large number of methods including, but not limited to, infection with viral vectors, liposome-based methods, biolistic particle acceleration (the gene gun), and naked DNA injection. Such therapeutically useful nucleic acids include, but are not limited to, coding sequences for full-length KCNB, coding sequences for a KCNB fragment, domain, derivative, or variant, KCNB antisense sequences, and KCNB ribozymes. Typically, such sequences will be operably linked to a promoter, but in numerous applications a nucleic acid will be administered to a cell that is itself directly therapeutically effective, e.g., certain antisense or ribozyme molecules.

The promoter used to direct expression of a heterologous nucleic acid depends on the particular application. The promoter is optionally positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the KCNB-encoding nucleic acid in host cells. A typical expression cassette thus contains a promoter operably linked to the nucleic acid sequence encoding a KCNB polypeptide, and signals required for efficient polyadenylation of the transcript, ribosome binding sites, and translation termination. The nucleic acid sequence encoding a KCNB polypeptide may be linked to a cleavable signal peptide sequence to promote secretion of the encoded protein by the transfected cell. Such signal peptides would include, among others, the signal peptides from tissue plasminogen activator, insulin, and neuron growth factor, and juvenile hormone esterase of *Heliothis virescens*. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as GST and LacZ. Epitope tags can also be added to recombinant proteins to provide convenient methods of isolation, e.g., c-myc, HA-tag, 6-His tag (SEQ ID NO:16), maltose binding protein, VSV-G tag, anti-DYKDDDDK (SEQ ID NO:17) tag, or any such tag, a large number of which are well known to those of skill in the art.

Expression vectors containing regulatory elements from eukaryotic viruses are typically used in eukaryotic expression vectors, e.g., SV40 vectors, papilloma virus vectors, and vectors derived from Epstein-Barr virus. Other exemplary eukaryotic vectors include pMSG, pAV009/A$^+$, pMTO10/A$^+$, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Some expression systems have markers that provide gene amplification, such as neomycin, thymidine kinase, hygromycin B phosphotransferase, and dihydrofolate reductase. Alternatively, high yield expression systems not involving gene amplification are also suitable, such as using a baculovirus vector in insect cells, with a sequence encoding a KCNB polypeptide under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are optionally chosen such that they do not interfere with the replication of the DNA in eukaryotic cells, if necessary.

Standard transfection methods are used to produce bacterial, mammalian, yeast or insect cell lines that express large quantities of a KCNB protein, which are then purified using standard techniques (see, e.g., Colley et al., *J. Biol. Chem.* 264:17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well known procedures for introducing foreign nucleotide sequences into host cells may be used. These include the use of reagents such as Superfect (Qiagen), liposomes, calcium phosphate transfection, polybrene, protoplast fusion, electroporation, microinjection, plasmid vectors, viral vectors, biolistic particle acceleration (the gene gun), or any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing a KCNB gene.

After the expression vector is introduced into the cells, the transfected cells are cultured under conditions favoring expression of the KCNB polypeptide, which is recovered from the culture using standard techniques identified below. Methods of culturing prokaryotic or eukaryotic cells are well known and are taught, e.g., in Ausubel et al., Sambrook et al., and in Freshney, *Culture of Animal Cells,* 3d. Ed., (1993), A Wiley-Liss Publication.

IV. Purification of KCNB Polypeptides

Either naturally occurring or recombinant KCNB polypeptides can be purified for use in functional assays, binding assays, diagnostic assays, and other applications. Naturally occurring KCNB polypeptides are purified, e.g., from mammalian tissue such as blood, lymphatic tissue, or any other source of a KCNB homolog. Recombinant KCNB polypeptides are purified from any suitable bacterial or eukaryotic expression system, e.g., CHO cells or insect cells.

KCNB proteins may be purified to substantial purity by standard techniques, including, but not limited to selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant KCNB polypeptide is being purified. For example, proteins having established molecular adhesion properties can be reversibly fused to the KCNB polypeptide. With the appropriate ligand, a KCNB polypeptide can be selectively adsorbed to a purification column and then freed from the column in a relatively pure form. The fused protein is then removed by enzymatic activity. KCNB proteins can also be purified using immunoaffinity columns.

A. Purification of Recombinant KCNB Protein

Recombinant proteins are expressed by transformed bacteria or eukaryotic cells such as CHO cells or insect cells in large amounts, typically after promoter induction but expression can be constitutive. Promoter induction with IPTG is one example of an inducible promoter system. Cells are grown according to standard procedures in the art. Fresh or frozen cells are used for isolation of protein.

Proteins expressed in bacteria may form insoluble aggregates ("inclusion bodies"). Several protocols are suitable for purification of KCNB inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to, urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate) and 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. KCNB polypeptides are separated from other bacterial proteins by standard separation techniques, e.g., with Ni-NTA agarose resin.

Alternatively, it is possible to purify KCNB polypeptides from bacteria periplasm. After lysis of the bacteria, when a KCNB protein is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying KCNB Polypeptides

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a KCNB protein can be used to isolated it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

KCNB proteins can also be separated from other proteins on the basis of their size, net surface charge, hydrophobicity, and affinity for heterologous molecules. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

V. Antibodies to KCNB Family Members

In numerous embodiments of the present invention, antibodies that specifically bind to KCNB polypeptides will be used. Such antibodies have numerous applications, including for the modulation of KCNB activity and for immunoassays to detect KCNB, and variants, derivatives, fragments, etc. of KCNB. Immunoassays can be used to qualitatively or quantitatively analyze the KCNB polypeptide. A general overview of the applicable technology can be found in Harlow & Lane, *Antibodies: A Laboratory Manual* (1988). In some embodiments, antibodies are used to detect KcNB for diagnostic and/or prognostic applications.

An antibody to KCNB can also comprise a chimeric antibody in which the antibody or a subfragment thereof is linked to a molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. Such antibodies can be usefully, for example, as targeting reagents to target a moiety such as a toxin to a KCNB-expressing cell.

Methods of producing polyclonal and monoclonal antibodies that react specifically with KCNB polypeptides are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341:544-546 (1989)).

A number of KCNB-comprising immunogens may be used to produce antibodies specifically reactive with a KCNB polypeptide. For example, a recombinant KCNB protein, or an antigenic fragment thereof, is isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the KCNB polypeptide. When appropriately high titers of antibody to the immunogen are obtained, blood is collected from the animal and antisera are prepared. Further fractionation of the antisera to enrich for antibodies reactive to the protein can be done if desired (see Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see Kohler & Milstein, *Eur. J Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of $10^4$ or greater are selected and tested for their cross reactivity against non-KCNB proteins, or even related proteins from other organisms, using a competitive binding immunoassay. Specific polyclonal antisera and monoclonal antibodies will usually bind with a $K_d$ of at least about 0.1 mM, more usually at least about 1 µM, optionally at least about 0.1 µM or better, and optionally 0.01 µM or better.

A. Immunological Binding Assays

Once KCNB-specific antibodies are available, individual KCNB proteins can be detected by a variety of immunoassay methods. For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Moreover, the immnunoassays of the present invention can be performed in any of several configurations, which are reviewed extensively in *Enzyme Immunoassay* (Maggio, ed., 1980); and Harlow & Lane, supra. Immunological binding assays (or immunoassays) typically use an antibody that specifically binds to a protein or antigen of choice (in this case a KCNB protein or an antigenic subsequence thereof). The antibody (e.g., anti-KCNB) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled KCNB polypeptide or a labeled anti-KCNB antibody. Alternatively, the labeling agent may be a third moiety, such a secondary antibody, that specifically binds to the antibody/KCNB complex (a secondary antibody is typically specific to antibodies of the species from which the first antibody is derived). Other proteins capable of specifically binding immunoglobulin constant regions, such as protein A or protein G, may also be used as the label agent. These proteins exhibit a strong nonimmunogenic reactivity with immunoglobulin constant regions from a variety of species (see, e.g., Kronval et al., *J. Immunol.* 111:1401-1406 (1973); Akerstrom et al., *J. Immunol.* 135: 2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

1. Noncompetitive Assay Formats

Immunoassays for detecting a KCNB protein in a sample may be either competitive or noncompetitive. Noncompetitive immunoassays are assays in which the amount of antigen is directly measured. In one preferred "sandwich" assay, for example, the anti-KCNB antibodies can be bound directly to a solid substrate on which they are immobilized. These immobilized antibodies then capture the KCNB protein present in the test sample. The KCNB protein thus immobilized is then bound by a labeling agent, such as a second KCNB antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

2. Competitive Assay Formats

In competitive assays, the amount of KCNB protein present in the sample is measured indirectly by measuring the amount of a known, added (exogenous) KCNB protein displaced (competed away) from an anti-KCNB antibody by the unknown KCNB protein present in a sample. In one competitive assay, a known amount of KCNB protein is added to a sample and the sample is then contacted with an antibody that specifically binds to the KCNB protein. The amount of exogenous KCNB protein bound to the antibody is inversely proportional to the concentration of KCNB protein present in the sample. In a particularly preferred embodiment, the antibody is immobilized on a solid substrate. The amount of KCNB protein bound to the antibody may be determined either by measuring the amount of KCNB protein present in a KCNB/antibody complex, or alternatively by measuring the amount of remaining uncomplexed protein. The amount of KCNB protein may be detected by providing a labeled KCNB molecule.

A hapten inhibition assay is another preferred competitive assay. In this assay, the known KCNB protein is immobilized on a solid substrate. A known amount of anti-KCNB antibody is added to the sample, and the sample is then contacted with the immobilized KCNB. The amount of anti-KCNB antibody bound to the known immobilized KCNB protein is inversely proportional to the amount of KCNB protein present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

3. Cross-Reactivity Determinations

Immunoassays in the competitive binding format can also be used for crossreactivity determinations. For example, a protein at least partially encoded by SEQ ID NO:2 can be immobilized to a solid support. Proteins (e.g., KCNB proteins and homologs) are added to the assay that compete for binding of the antisera to the immobilized antigen. The ability of the added proteins to compete for binding of the antisera to the immobilized protein is compared to the ability of the KCNB polypeptide encoded by SEQ ID NO:2 to compete with itself. The percent cross-reactivity for the above proteins is calculated, using standard calculations. Those antisera with less than 10% cross-reactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a KCNB protein, to the immunogen protein (i.e., KCNB protein encoded by SEQ ID NO:2). In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the protein encoded by SEQ ID NO:2 that is required to inhibit 50% of binding, then the second protein is said to specifically bind to the polyclonal antibodies generated to a KCNB immunogen.

Polyclonal antibodies that specifically bind to a KCNB protein from a particular species can be make by subtracting out cross-reactive antibodies using KCNB homologs. For example, antibodies specific to human KCNB can be made by subtracting out antibodies that are cross-reactive with mouse KCNB. In an analogous fashion, antibodies specific to a particular KCNB protein can be made in an organism with multiple KCNB genes.

4. Other Assay Formats

Western blot (immunoblot) analysis is used to detect and quantify the presence of KCNB protein in a sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the KCNB protein. The anti-KCNB polypeptide antibodies specifically bind to the KCNB polypeptide on the solid support. These antibodies may be directly labeled or alternatively may be subsequently detected using labeled antibodies (e.g., labeled sheep anti-mouse antibodies) that specifically bind to the anti-KCNB antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

One of skill in the art will appreciate that it is often desirable to minimize nonspecific binding in immunoassays. Particularly, where the assay involves an antigen or antibody immobilized on a solid substrate it is desirable to minimize the amount of nonspecific binding to the substrate. Means of reducing such nonspecific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

5. Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADSTM), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Nonradioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize a KCNB protein, or secondary antibodies that recognize anti-KCNB.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see, U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple colorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

VI. Diagnosis of Diseases Associated with Altered KCNB Activity or Expression KCNB nucleic acids, proteins, and/or antibodies can be used diagnostically or prognostically to detect diseases or conditions associated with altered KCNB activity or expression relative to normal. Such diseases can be associated with either decreased or increased KCNB activity or expression. KCNB activity or expression can be detected using any of a variety of reagents including, for example, KCNB protein, mRNA, genomic DNA, or antibodies to KCNB. Changes in activity can indicate alterations in, e.g., KCNB gene copy number, mutations in the KCNB gene sequence, alterations in transcription, translation, RNA, protein level, protein stability, or protein activity. Accordingly, any of a large number of assays, examples of which are provided herein, can be used to detect the KCNB nucleic acids or polypeptides.

Accordingly, the present sequences can be used to treat any of the herein-described disorders or conditions in a patient, wherein an alteration in the level of expression or activity KCNB, or the detection of a deleterious mutation in a KCNB polynucleotide or polypeptide, indicates the presence or the likelihood of the disease or condition. Thus, the present invention provides methods of detecting or diagnosing diseases or the likelihood of disease for diseases that are associated with increased or decreased activity of KCNB. These include cancer (further discussed below) brain-associated disorders such as epilepsy, Alzheimer disease, Parkinson's disease, stroke, multiple, sclerosis, migraine, and psychiatric disorder including depression, schizophrenia, bipolar disease as well as others (see, e.g., *Harrison's Principles of Internal Medicine*, 12th Edition, Wilson, et al., eds., McGraw-Hill, Inc.). Other diseases include diseases related to the heart, such as arrhythmias, heart failure, and various vascular diseases (see, e.g., *Harrison's Principles of Internal Medicine*, 12th Edition, Wilson, et al., eds., McGraw-Hill, Inc.) and diseases related to the pancreas such as pancreatitis, diabetes, other abnormalities of hormonal secretion in the pancreas, e.g., glucagon, somatostatin secretion (see, e.g., *Harrison's Principles of Internal Medicine*, 12th Edition, Wilson, et al., eds., McGraw-Hill, Inc).

In certain embodiments, e.g., diagnosis of cancer, the level of KCNB polynucleotide, polypeptide, or protein activity will be quantified. In such embodiments, the difference between the level of KCNB in a biological sample from a patient having, or suspected of having a KCNB-associated disorder, and a normal, control level will preferably be statistically significant. Typically, a diagnostic presence often represents at least about a 1.5, 2, 5, 10, or greater fold alteration in the level of KCNB polypeptide or polynucleotide in the biological sample compared to a level expected in a control sample, such as a sample of biological material representative of a healthy subject or normal tissue. Detection of KCNB can be performed in vitro, i.e., in cells within a biological sample taken from the mammal, or in vivo. A "diagnostic presence" indicates any level of KCNB that is altered from that expected in a normal control sample.

In one embodiment, a KCNB nucleic acid or protein can be used as a diagnostic or prognostic tool, alone or in combination with other diagnostic methods, to detect increases in KCNB copy number or expression that are associated with cancer, e.g., breast or lung as well as other cancers such as epithelial cancers, e.g., colorectal, prostate, kidney, stomach, bladder, ovarian, or a cancer of the gastrointestinal tract. The detection of KCNB nucleic acids or proteins can also be used to monitor the efficacy of a cancer treatment. For example, the level of KCNB protein or nucleic acid after an anti-cancer treatment can be compared to the level before treatment, wherein a decrease in the level of the KCNB protein or nucleic acid after the treatment indicates efficacious treatment. The levels of KCNB protein or nucleic acid can also be used to influence the choice of anti-cancer treatment in a mammal, where, for example, a large increase in KCNB indicates the use of a more aggressive anti-cancer therapy, and a small increase or no increase indicates the use of a less aggressive anti-cancer therapy. In addition, the ability to detect cancer cells that exhibit altered KCNB activity or expression can be useful in monitoring, e.g., in vivo or in vitro, the number and/or location of cancer cells in a patient in order to assess the progression of the disease over time.

VII. Modulating KCNB Activity

A. Assays for Modulators of KCNB Proteins

In numerous embodiments of this invention, the level of KCNB activity will be modulated in a cell by administering to the cell, in vivo or in vitro, any of a large number of KCNIB-modulating molecules, e.g., polypeptides, antibodies, amino acids, nucleotides, lipids, carbohydrates, or any organic or inorganic molecule.

To identify molecules capable of modulating KCNB, assays will be performed to detect the effect of various candidate modulators on KCNB activity in a cell. The activity of KCNB polypeptides can be assessed using a variety of in vitro and in vivo assays to determine functional, chemical, and physical effects, e.g., measuring the binding of KCNB to other molecules (e.g., radioactive binding), measuring KCNB protein and/or RNA levels, or measuring other aspects of KCNB polypeptides, e.g., phosphorylation levels, transcription levels, the ability to protect cells from apoptosis (programmed cell death), receptor or channel activity, and the like. Such assays can be used to test for both activators and inhibitors of KCNB proteins. Modulators thus identified are useful for, e.g., many diagnostic and therapeutic applications.

The potassium channcel activity of KCNB proteins can be assayed using a variety of assays to measure changes in ion fluxes including patch clamp techniques, measurement of whole cell currents, radiolabeled rubidium flux assays, and fluorescence assays using voltage-sensitive dyes (see, e.g., Vestergarrd-Bogind et al., *J. Membrane Biol.* 88:67-75 (1988); Daniel et al., *J. Pharmacol. Meth.* 25:185-193 (1991); Hoevinsky et al., *J. Membrane Biol.* 137:59-70 (1994)). For example, a nucleic acid encoding a KCNB protein or homolog thereof can be injected into Xenopus oocytes. KCNB activity can then be assessed by measuring changes in membrane polarization, i.e., changes in membrane potential. A preferred means to obtain electrophysiological measurements is by measuring currents using patch clamp techniques, e.g., the "cell-attached" mode, the "inside-out" mode, and the "whole cell" mode (see, e.g., Ackerman et al., *New Engl. J. Med.* 336:1575-1595, 1997). Whole cell currents can be determined using standard methodology such as that described by Hamil et al., *PFlugers. Archiv.* 391:185 (1981).

KCNB activity, such as protection from apoptosis, can also be assessed. For example, the ability of KCNB to protect cells from TNF-α induced programmed cell death can be measured using methodology described in Example 4.

The KCNB protein of the assay will typically be a recombinant or naturally occurring polypeptide with a sequence of SEQ ID NO:1 or a conservatively modified variant thereof Alternatively, the KCNB protein of the assay will be derived from a eukaryote and include an amino acid subsequence having amino acid sequence identity to SEQ ID NO:1. Generally, the amino acid sequence identity will be at least 70%, optionally at least 75%, 85%, or 90%; or optionally at least 95% to 98%. Optionally, the polypeptide of the assays will comprise a domain of a KCNB protein, such as an N-terminal domain, a C-terminal domain, an extracellular loop, one or more transmembrane domains, and the like. In certain embodiments, a domain of a KCNB protein, e.g., an N-terminal domain, a C-terminal domain, an extracellular loop, or one or more transmembrane domains, is bound to a solid substrate and used, e.g., to isolate any molecules that can bind to and/or modulate their activity. In certain embodiments, a domain of a KCNB polypeptide, e.g., an N-terminal domain, a C-terminal domain, an extracellular loop, or one or more transmembrane domains, is fused to a heterologous polypeptide, thereby forming a chimeric polypeptide. Such chimeric polypeptides are also useful, e.g., in assays to identify modulators of KCNB.

Samples or assays that are treated with a potential KCNB protein inhibitor or activator are compared to control samples without the test compound, to examine the extent of modulation. Control samples (untreated with activators or inhibitors) are assigned a relative KCNB activity value of 100. Inhibition of a KCNB protein is achieved when the KCNB activity value relative to the control is about 90%, optionally about 50%, optionally about 25-0%. Activation of a KCNB protein is achieved when the KCNB activity value relative to the control is about 110%, optionally about 150%, 200-500%, or about 1000-2000%.

The effects of the test compounds upon the function of the polypeptides can be measured by examining any of the parameters described above. Any suitable physiological change that affects KCNB activity can be used to assess the influence of a test compound on the polypeptides of this invention. When the functional consequences are determined using intact cells or animals, one can also measure a variety of effects such as changes in cell growth or pH changes, changes in intracellular second messengers such as $Ca^{2+}$, IP3, cGMP, or cAMP, or changes in the membrane potential of cells.

A host cell containing a KCNB protein of interest is contacted with a test compound for a sufficient time to effect any interactions, and then the level of gene expression is measured. The amount of time to effect such interactions may be empirically determined, such as by running a time course and measuring the level of transcription as a function of time. The amount of transcription may be measured using any method known to those of skill in the art to be suitable. For example, mRNA expression of the protein of interest may be detected using Northern blots or by detecting their polypeptide products using immunoassays.

B. Assays for KCNB-Interacting Compounds

In certain embodiments, assays will be performed to identify molecules that physically interacting with KCNB proteins. Such molecules can be any type of molecule, including polypeptides, polynucleotides, amino acids, nucleotides, carbohydrates, lipids, or any other organic or inorganic molecule. Such molecules may represent molecules that normally interact with KCNB or may be synthetic or other molecules that are capable of interacting with KCNB and that can potentially be used as lead compounds to identify classes of molecules that can interact with and/or modulate KCNB. Such assays may represent physical binding assays, such as affinity chromatography, immunoprecipitation, two-hybrid screens, or other binding assays, or may represent genetic assays.

In any of the binding or functional assays described herein, in vivo or in vitro, any KCNB protein, or any derivative, variation, homolog, or fragment of a KCNB protein, can be used. Preferably, the KCNB protein is at least about 70% identical to SEQ ID NO:1. In numerous embodiments, a fragment of a KCNB protein is used. For example, a fragment that contains only an N-terminal or C-terminal domain, or an extracellular loop or transmembrane domain can be used. Such fragments can be used alone, in combination with other KCNB fragments, or in combination with sequences from heterologous proteins, e.g., the fragments can be fused to a heterologous polypeptides, thereby forming a chimeric polypeptide.

Compounds that interact with KCNB proteins can be isolated based on an ability to specifically bind to a KCNB protein or fragment thereof. In numerous embodiments, the KCNB protein or protein fragment will be attached to a solid support. In one embodiment, affinity columns are made using the KCNB polypeptide, and physically-interacting molecules are identified. It will be apparent to one of skill that chromatographic techniques can be performed at any scale and using equipment from may different manufactures (e.g., Pharmacia Biotechnology). In addition, molecules that interact with KCNB proteins in vivo can be identified by co-immunoprecipitation or other methods, i.e., immunoprecipitating KCNB protein using anti-KCNB antibodies from a cell or cell extract, and identifying compounds, e.g., proteins, that are precipitated along with the KCNB protein. Such methods are well known to those of skill in the art and are taught, e.g., in Ausubel et al., Sambrook et al., and Harlow & Lane, all supra.

C. Modulators and Binding Compounds

The compounds tested as modulators of a KCNB protein can be any small organic or inorganic chemical compound, or a biological entity, such as a protein, sugar, nucleic acid or lipid. Typically, test compounds will be small chemical molecules and peptides. Essentially any chemical compound can be used as a potential modulator or binding compound in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, MO), Aldrich (St. Louis, Mo.), Sigma-Aldrich (St. Louis, Mo.), Fluka Chemika-Biochemica Analytika (Buchs, Switzerland) and the like.

In one preferred embodiment, high throughput screening methods involve providing a combinatorial chemical or peptide library containing a large number of potential therapeutic compounds (potential modulator or binding compounds). Such "combinatorial chemical libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J Pept. Prot. Res.* 37:487-493 (1991) and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 20 (1994)), oligocarbamates (Cho et al., Science 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology,* 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, Jan 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Tripos, Inc., St. Louis, Mo., 3D Pharmaceuticals, Exton, Pa., Martek Biosciences, Columbia, Md., etc.).

1. Solid State and Soluble High Throughput Assays

In one embodiment, the invention provides soluble assays using molecules such as an N-terminal or C-terminal domain either alone or covalently linked to a heterologous protein to create a chimeric molecule. In another embodiment, the invention provides solid phase based in vitro assays in a high throughput format, where a domain, chimeric molecule, KCNB protein, or cell or tissue expressing a KCNB protein is attached to a solid phase substrate.

In the high throughput assays of the invention, it is possible to screen up to several thousand different modulators in a single day. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100 to about 1500 different compounds. It is possible to assay several different plates per day; assay screens for up to about 6,000-20,000 different compounds is possible using the integrated systems of the invention. More recently, microfluidic approaches to reagent manipulation have been developed.

The molecule of interest can be bound to the solid state component, directly or indirectly, via covalent or non covalent linkage, e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly-Gly sequences of between about 5 and 200 amino acids (SEQ ID NO:18). Such flexible linkers are known to persons of skill in the art. For example, poly(ethelyne glycol) linkers are available from Shearwater Polymers, Inc. Huntsville, Ala. These linkers optionally have amide linkages, sulthydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Nonchemical approaches for fixing tag binders to substrates include other common methods, such as heat, cross-linking by UV radiation, and the like. 2. Computer-Based Assays Yet another assay for compounds that modulate KCNB protein activity involves computer assisted drug design, in which a computer system is used to generate a three-dimensional structure of a KCNB protein based on the structural information encoded by its amino acid sequence. The input amino acid sequence interacts directly and actively with a pre-established algorithm in a computer program to yield secondary, tertiary, and quaternary structural models of the protein. The models of the protein structure are then examined to identify regions of the structure that have the ability to bind. These regions are then used to identify compounds that bind to the protein.

The three-dimensional structural model of the protein is generated by entering protein amino acid sequences of at least 10 amino acid residues or corresponding nucleic acid sequences encoding a KCNB polypeptide into the computer system. The nucleotide sequence encoding the polypeptide, or the amino acid sequence thereof, is preferably SEQ ID NO:2 or SEQ ID NO:1, and conservatively modified versions thereof. The amino acid sequence represents the primary sequence or subsequence of the protein, which encodes the structural information of the protein. At least 10 residues of the amino acid sequence (or a nucleotide sequence encoding 10 amino acids) are entered into the computer system from computer keyboards, computer readable substrates that include, but are not limited to, electronic storage media (e.g., magnetic diskettes, tapes, cartridges, and chips), optical media (e.g., CD ROM), information distributed by internet sites, and by RAM. The three-dimensional structural model of the protein is then generated by the interaction of the amino acid sequence and the computer system, using software known to those of skill in the art.

The amino acid sequence represents a primary structure that encodes the information necessary to form the secondary, tertiary and quaternary structure of the protein of interest. The software looks at certain parameters encoded by the primary sequence to generate the structural model. These parameters are referred to as "energy terms," and primarily include electrostatic potentials, hydrophobic potentials, solvent accessible surfaces, and hydrogen bonding. Secondary energy terms include van der Waals potentials. Biological molecules form the structures that minimize the energy terms in a cumulative fashion. The computer program is therefore using these terms encoded by the primary structure or amino acid sequence to create the secondary structural model.

The tertiary structure of the protein encoded by the secondary structure is then formed on the basis of the energy terms of the secondary structure. The user at this point can enter additional variables such as whether the protein is membrane bound or soluble, its location in the body, and its cellular location, e.g., cytoplasmic, surface, or nuclear. These variables along with the energy terms of the secondary structure are used to form the model of the tertiary structure. In modeling the tertiary structure, the computer program matches hydrophobic faces of secondary structure with like, and hydrophilic faces of secondary structure with like.

Once the structure has been generated, potential modulator binding regions are identified by the computer system. Three-dimensional structures for potential modulators are generated by entering amino acid or nucleotide sequences or chemical formulas of compounds, as described above. The three-dimensional structure of the potential modulator is then compared to that of the KCNB protein to identify compounds that bind to the protein. Binding affinity between the protein and compound is determined using energy terms to determine which compounds have an enhanced probability of binding to the protein.

Computer systems are also used to screen for mutations, polymorphic variants, alleles and interspecies homologs of KCNB genes. Such mutations can be associated with disease states or genetic traits. As described above, GeneChip™ and related technology can also be used to screen for mutations, polymorphic variants, alleles and interspecies homologs. Once the variants are identified, diagnostic assays can be used to identify patients having such mutated genes. Identification of the mutated KCNB genes involves receiving input of a first nucleic acid or amino acid sequence of SEQ ID NO:2 or SEQ ID NO:1, respectively, and conservatively modified versions thereof. The sequence is entered into the computer system as described above. The first nucleic acid or amino acid sequence is then compared to a second nucleic acid or amino acid sequence that has substantial identity to the first sequence. The second sequence is entered into the computer system in the manner described above. Once the first and second sequences are compared, nucleotide or amino acid differences between the sequences are identified. Such sequences can represent allelic differences in various KCNB genes, and mutations associated with disease states and genetic traits.

VIII. Modulating nKCN Activity/Expression to Treat Diseases or Conditions

In numerous embodiments of this invention, a compound, e.g., nucleic acid, polypeptide, or other molecule is administered to a patient, in vivo or ex vivo, to effect a change in KCNB activity or expression in the patient. The desired change may be either an increase or a decrease in activity or expression of KCNB. For example, in a breast cancer patient with a tumor that exhibits increased levels of KCNB relative to normal breast tissue, it may be desirable to decrease the activity or expression of KCNB. In other patients with diseases associated with decreased activity or expression of KCNB, it may be desirable to increase the activity or expression of KCNB.

Thus, the present invention provides methods of treating diseases that are associated with increased or decreased activity of KCNB. In certain embodiments, KCNB can be used in the diagnosis and treatment of diseases or conditions. For example, the activity of KCNB that is expressed in a particular cell type can be used to modulate cellular function (e.g., responsiveness to extracellular signals), thereby specifically modulating the function of the cells of that type in a patient. Further, mutations in the cell specific KCNBs will likely produce a disease, condition, or symptom associated with a lack of function of the particular cell type. These include cancer, including breast, lung, colon, and prostate cancer, brain-associated disorders such as epilepsy, Alzheimer disease, Parkinson's disease, stroke, multiple, sclerosis, migraine, and psychiatric disorder including depression, schizophrenia, bipolar disease as well as others (see, e.g., *Harrison's Principles of Internal Medicine,* 12th Edition, Wilson, et al., eds., McGraw-Hill, Inc.). Other diseases include diseases related to the heart, such as arrhythmias, heart failure, and various vascular diseases (see, e.g., *Harrison's Principles of Internal Medicine,* 12th Edition, Wilson, et al., eds., McGraw-Hill, Inc.) and diseases related to the pancreas such as pancreatitis, diabetes, other abnormalities of hormonal secretion in the pancreas, e.g., glucagon, somatostatin secretion (see, e.g., *Harrison's Principles of Internal Medicine,* 12th Edition, Wilson, et al., eds., McGraw-Hill, Inc). Accordingly, modulation of KCNB (e.g., by administering modulators of KCNB) can be used to treat or prevent any of the conditions or diseases.

Compounds that can be administered to a patient include nucleic acids encoding full length KCNB polypeptides, e.g., as shown as SEQ ID NO:1, or any derivative, fragment, or variant thereof, operably linked to a promoter. Suitable nucleic acids also include inhibitory sequences such as antisense or ribozyme sequences, which can be delivered in, e.g., an expression vector operably linked to a promoter, or can be delivered directly. Also, any nucleic acid that encodes a polypeptide that modulates the expression of KCNB can be used.

In general, nucleic acids can be delivered to cells using any of a large number of vectors or methods, e.g., retroviral, adenoviral, or adeno-associated virus vectors, liposomal formulations, naked DNA injection, facilitated (bupivicaine, polymers, peptide-mediated) delivery, cationic lipid complexes, and particle-mediated ("gene gun") or pressure-mediated delivery.

Proteins can also be delivered to a patient to modulate KCNB activity. In preferred embodiments, a polyclonal or monoclonal antibody that specifically binds to KCNB will be delivered. In addition, any polypeptide that interacts with and/or modulates KCNB activity can be used, e.g., a polypeptide that is identified using the presently described assays. In addition, polypeptides that affect KCNB expression can be used.

Further, any compound that is found to or designed to interact with and/or modulate the activity of KCNB can be used. For example, any compound that is found, using the methods described herein, to bind to or modulate the activity of KCNB can be used.

Any of the above-described molecules can be used to increase or decrease the expression or activity of KCNB, or to otherwise affect the properties and/or behavior of KCNB polypeptides or polynucleotides, e.g., stability, intracellular localization, interactions with other intracellular or extracellular moieties, etc.

A. Administration and Pharmaceutical Compositions

Administration of any of the present molecules can be achieved by any of the routes normally used for introducing or bringing a modulator compound into ultimate contact with the tissue to be treated. The modulators are administered in any suitable manner, optionally with pharmaceutically acceptable carriers. Suitable methods of administering such modulators are available and well known to those of skill in the art, and, although more than one route can be used to administer a particular composition, a particular route can often provide a more immediate and more effective reaction than another route.

Pharmaceutically acceptable carriers are determined in part by the particular composition being administered, as well as by the particular method used to administer the composition. Accordingly, there is a wide variety of suitable formulations of pharmaceutical compositions of the present invention (see, e.g., *Remington's Pharmaceutical Sciences,* 17th ed. 1985)).

The KCNB modulators, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for administration include aqueous and nonaqueous solutions, isotonic sterile solutions, which can contain antioxidants, buffers, bacteriostats, and solutes that render the formulation isotonic, and aqueous and non-aqueous sterile suspensions that can include suspending agents, solubilizers, thickening agents, stabilizers, and preservatives. In the practice of this invention, compositions can be administered, for example, orally, nasally, topically, intravenously, intraperitoneally, intravesically or intrathecally. The formulations of compounds can be presented in unit-dose or multi-dose sealed containers, such as ampules and vials. Solutions and suspensions can be prepared from sterile powders, granules, and tablets of the kind previously described. The modulators can also be administered as part a of prepared food or drug.

The dose administered to a patient, in the context of the present invention should be sufficient to effect a beneficial response in the subject over time. The dose will be determined by the efficacy of the particular modulators employed and the condition of the subject, as well as the body weight or surface area of the region to be treated. The size of the dose also will be determined by the existence, nature, and extent of any adverse side-effects that accompany the administration of a particular compound or vector in a particular subject.

In determining the effective amount of the modulator to be administered, a physician may evaluate circulating plasma levels of the modulator, modulator toxicities, and the production of anti-modulator antibodies. In general, the dose equivalent of a modulator is from about 1 ng/kg to 10 mg/kg for a typical subject.

For administration, modulators of the present invention can be administered at a rate determined by the LD-50 of the modulator, and the side-effects of the compound at various concentrations, as applied to the mass and overall health of the subject. Administration can be accomplished via single or divided doses.

IX. Kits

Reagents that specifically hybridize to KCNB nucleic acids, such as KCNB probes and primers, and KCNB-specific reagents that specifically bind to or modulate the activity of a KCNB protein, e.g., KCNB antibodies or other compounds are used to treat KCNB-associated diseases or conditions.

Nucleic acid assays for detecting the presence of DNA and RNA for a KCNB polynucleotide in a sample include numerous techniques known to those skilled in the art, such as Southern analysis, Northern analysis, dot blots, RNase protection, SI analysis, amplification techniques such as PCR and LCR, and in situ hybridization. In in situ hybridization, for example, the target nucleic acid is liberated from its cellular surroundings so as to be available for hybridization within the cell while preserving the cellular morphology for subsequent interpretation and analysis. The following articles provide an overview of the art of in situ hybridization: Singer et al., *Biotechniques* 4:230-250 (1986); Haase et al., *Methods in Virology, vol. VII*, pp. 189-226 (1984); and *Nucleic Acid Hybridization: A Practical Approach* (Hames et al., eds. 1987). In addition, a KCNB protein can be detected using the various immunoassay techniques described above. The test sample is typically compared to both a positive control (e.g., a sample expressing a recombinant KCNB protein) and a negative control.

The present invention also provides for kits for screening for modulators of KCNB proteins or nucleic acids. Such kits can be prepared from readily available materials and reagents. For example, such kits can comprise any one or more of the following materials: KCNB nucleic acids or proteins, reaction tubes, and instructions for testing KCNB activity. Optionally, the kit contains a biologically active KCNB protein. A wide variety of kits and components can be prepared according to the present invention, depending upon the intended user of the kit and the particular needs of the user.

EXAMPLES

Example 1

Amplification of KCNB in Cancer

The following example shows that KCNB is amplified in cancer.

KCNB was identified as the epicenter of amplification at human chromosomal region 8q24.3, which is amplified in cancer. This example demonstrates determination of DNA copy number in the 8q24.3 amplicon (FIG. 2).

DNA copy number was determined for each of 10 markers in genomic DNA samples prepared from both primary tumors and tumor cell lines to define the boundaries of the amplicon. The following markers were used: Wi-1 1623, human STS; FAK, focal adhesin kinase (Accession No. L13616); 34D10-51, T7 side BAC sequence of clone 34D10 of CITB human BAC B&C libraries release IV; 381K12-T7, T7 side BAC sequence of clone 381K12 of CITB human BAC B&C libraries release IV; 431C18T7, T7 side BAC end sequence of genomic clone AC007869; d8s1741, human STS; 564L17-5', T7 end BAC sequence of genomic clone AC007871; 4P6-3', SP6 end BAC sequence of genomic clone 4p6 of CITB human BAC B&C libraries release IV; WI-1 8632, human STS; T1-5',5' end of human cDNA clone AK026394.1. CHTN159 and 87-634 are primary breast tumors and ZR7530 and MDAMB436 are breast tumor cell lines.

Probes for each marker were designed using PrimerExpress 1.0 (Applied Biosystems)and synthesized by Operon Technologies. Target probe, a reference probe representing a normal single copy region in the genome, and tumor genomic DNA (10 ng) were subjected to the Applied Biosystems 7700 Taqman Sequence Detector following the manufacturer's protocol. The results are shown in FIG. 2. These data define the boundaries of amplification of the 8q24.3 region.

Further analysis of approximately 200 breast tumors showed that about 10-14% are amplified at this region. Primary breast tumors were provided by Linda Rodgers and Mike Wigler at the Cold Spring Harbor Laboratory and by Jeff Marks at Duke University Identification of KCNB The PCR-based physical mapping, supra, showed that the BAC clone 431 c 18 (Accession number AC007869) of human BAC library CITB release IV (Research Genetics) was in the epicenter. Subsequently, a human genomic sequence of about 200 kB in length that is contained in the BAC clone was used to search the Genbank and SWISSPROT databases via BLASTX.

Regions of the sequence were found to exhibit sequence homology with a previously Caenorhabditis elegans K$^+$ channel protein TWK-8 (Accession number P34410.) TWK-8 is homologous to a cloned human potassium channel, KCNK3 (Accession number AAC51777/PID g2465542), which is localized to human chromosome 2p23. Based on the homology to KCNK3, an open reading frame set out as SEQ ID NO:2 was determined from the genomic sequence. The deduced open reading frame of KCNB shares 62% amino acid identity with KCNK3. The predicted amino acid sequence of the KCNB protein encoded by genomic DNA is shown as SEQ ID NO:1.

PCR Amplification of KCNB cDNA from Breast Tumor Cell Line

High fidelity PCR employing primers with the nucleotide sequences set out in SEQ ID NOs:3 and 4 was then performed to obtain a EDNA encoding KCNB from a cDNA preparation from a breast cancer cell line ZR7530. The cDNA was isolated as follows.

(1) 1st Strand cDNA Preparation:

One micro-gram of total RNA prepared from a human breast cancer cell line, ZR7530, was incubated with 1 µM of oligo (dT)$_{18}$ and 200 units of MMLV reverse transcriptase (ClONTECH, Palo Alto, Calif.) in a total volume of 20 µL containing the following components: 50 mM Tris-HCl pH 8.3, 75 mM KCl, 3 mM MgCl$_2$ and 50 µM dNTP. After an incubation of 60 min at 42° C., the reaction was maintained at 95° C. for 5 min to inactivate the reverse transcriptase. Subsequently, eighty micro-liters of nuclease-free water was added to give the final 1$^{st}$-strand cDNA preparation.

(2) PCR Amplification of KCN cDNA:

Four micro-liters of the 1 st strand cDNA preparation of ZR7530 was mixed in a total volume of 50 µL with the following ingredients: 20 µM dNTP, 0.5 µof each of oligonucleotides R5 and R10 (SEQ ID NOs: 3 and 4, respectively), 10 mM Tris-HCl pH 8.85, 5 mM (NH$_4$)2SO$_4$, 25 mM KCl, 2 mM MgSO$_4$, and 3 units of PWO DNA polymerase (Roche, Indianapolis, Ind.). The reaction was then overlaid with mineral oil (30 µL) and amplified using a PCR thermal cycler (MJ Research, Watertown, Mass.) for 40 cycles, each consisting of 3 steps: 95° C. for 20 sec, 64° C. for 40 sec, and 72° C. for 1 min. Subsequently, the mixture was purified using High-Pure PCR purification columns (Roche, Indianapolis, Ind.) following manufacturer's recommendations. Upon analyses using 2% agarose gel electrophoresis, a product of approximately 1.2 kb in length was detected, representing the full-length open reading frame of KCNB.

The sequence of the cDNA was identical to that of the open reading frame of the genomic sequence (SEQ ID NO:2) except for a cytosine at position 653, which replaced the T present in the genomic sequence. The substitution of C for T at that position does not alter the amino acid encoded by the nucleotide sequence. The nucleotide sequence of the 5' and 3' untranslated regions (UTRs) of the KCNB messenger RNA in the breast tumor cell line ZR7530 were determined using the RACE (rapid amplification of cDNA ends) method. The cDNA sequence including the 5' and 3' UTRs is set forth in SEQ ID NO:5.

The sequence including the 5' and 3' UTRs is about 2.3 kb in length. The starting methionine codon and the stop codon are indicated in bold. The G nucleotide at position 323 from the 5' end of the sequence marks the end the exon 1 and G nucleotide at position 324 represents the first base of exon 2. From the comparison of KCNB cDNA and the corresponding genomic sequence (accession #:AC007869), an intron of approximately 83.6 kb is deduced to be flanked by exon 1 and 2. The putative polyadenylation signal sequence is underlined.

Example 2

KCNB Expression

The following examples demonstrates that KCNB is normally expressed at high levels in the brain and is overexpressed in cancer.

KCNB is Overexpressed in a Breast Cancer Cell Line Relative to Normal Breast Cells The level of expression of KCNB mRNA was also determined in breast cancer tissue relative to normal breast tissue (Table 1). Quantitative PCR was performed as indicated below.

Total RNA was isolated from tumor cell lines and frozen primary tumor tissues using the Trizol reagent (Gibco/Life technology, Gaithersburg, Md.) and stored in RNAsecure (Ambion, Austin, Tex.) at about 1 µg/µL concentration. Total RNA was treated with DNAaseI (Gibco) to eliminate genomic DNA and then subjected to reverse transcriptase reaction coupled with PCR amplification in a one-tube format according to the manufacturer (Perkin Elmer/ABI). The number of PCR cycles needed to cross a preset threshold, also known as Ct value, in the sample tumor RNA preparations and a series of normal mammary gland RNA preparations at various concentrations was measured for both the target probe and the β-actin probe by using a PE/ABI 7700 Taqman machine. The relative abundance of target sequence to β-actin in each sample was then calculated by statistical analyses of the Ct values of the unknown samples and the standard curve generated from the mammary gland RNA preps of various concentrations.

Three oligonucleotides were used for each quantitative PCR: a forward primer, a reverse primer, and a probe. In performing the analyses to obtain the results shown in Table 1, two different sets of oligonucleotides, which are set out in SEQ ID NOs 6-8 and 9-11, were used. Comparable results were obtained with each set. The results shown in Table 1 demonstrate that KCNB is overexpressed in breast cancer cells relative to normal.

Out of the 38 primary breast tumors examined, 19 express KCNB mRNA at a level 5-fold or greater than normal breast tissue (19/38=50% overexpression frequency) (Table 1b). All 11 tumors showing KCNB gene copy number increases also showed overexpression of the mRNA. (Tumors exhibiting a KCNB gene copy number less than 2.5 are labeled "−" and tumors with a copy number greater than 2.5 are labeled "+". ND stands for "not determined".)

Of the 12 tumors that do not exhibit amplification of KCNB, 7 overexpressed KCNB, often a hallmark of an oncogene.

TABLE 1a

Relative KCNB mRNA Levels In Breast Cancer CellLines

| Breast Tumor Cell Line | Relative mRNA Level |
| --- | --- |
| [1]ZR7530 | 3 |
| BT20 | 0.27 |
| BT549 | 0.81 |
| MCF7 | 0.32 |
| 2 6NC | 0.56 |
| [2]HBL-100 | 1 |
| [2]Normal mammary gland epithelial cells | 1 |

[1]Of the 7 cell lines in the table, ZR7530 is the only one amplified at 8q24.3.
[2]Relative levels of KCNB mRNA were normalized to either the HBL-100 cell line or to normal mammary gland epithelial cells. β-actin mRNA was used as the internal reference in all samples tested.
ND = not determined TABLE 1b mRNA Expression in Primary Breast Tumors

| Breast tumor | Gene copy number | Relative mRNA expression level |
|---|---|---|
| 88-523 | − | 7.1 |
| 96-201 | − | 13 |
| 96-342 | − | 5.8 |
| 96-102 | − | 8.9 |
| 96-32 | − | 0.4 |
| 96-16 | − | 0.7 |
| 95-523 | − | 1.0 |
| 95-377 | − | 3.5 |
| 95-326 | − | 10 |
| 94-847 | − | 2.9 |
| 94-797 | − | 16 |
| 88-468 | − | 27 |
| CHTN159 | + | 13.8 |
| 95-480 | + | 9.2 |
| 95-347 | + | 11 |
| 91-82 | + | 550 |
| 90-445 | + | 32.3 |
| 90-794 | + | 343.3 |
| 90-197 | + | 66 |
| 88-499 | + | 108 |
| 87-634 | + | 69 |
| 96-308 | + | 25 |
| 88-682 | + | 3.5 |
| 96-442 | ND | 2.2 |
| 96-349 | ND | 4.7 |
| 96-317 | ND | 11 |
| 96-273 | ND | 0.4 |
| 96-190 | ND | 5.2 |
| 96-160 | ND | 1.2 |
| 96-140 | ND | 3.4 |
| 96-109 | ND | 0.35 |
| 96-84 | ND | 1.0 |
| 95-504 | ND | 1.9 |
| 95-487 | ND | 1.5 |

TABLE 1b-continued mRNA Expression in Primary Breast Tumors

| Breast tumor | Gene copy number | Relative mRNA expression level |
|---|---|---|
| 95-427 | ND | 1.4 |
| 95-283 | ND | 1.7 |
| 95-237 | ND | 1.6 |
| 95-65 | ND | 0.14 |

KCNB is Expressed in other Epithelial Tumors.

KCNB expression was also examined in tumor types other than breast tumor (Table 2). The results show that KCNB is also overexpressed in lung and prostate tumors. The number of each tumor type examined is indicated. Four metastatic prostate tumors were found to overexpress KCNB at 5-fold or greater out of 26 samples examined. Of 20 lung tumors examined, 35% exhibited expression greater than five fold.

TABLE 2

| Tumor Type | Amplification | mRNA overexpression frequency |
|---|---|---|
| Breast Tumors n = 38 | <2-fold: 19<br>5-10-fold: 7<br>10-20-fold: 6<br>>20-fold: 6 | 50% > 5-fold |
| Lung Tumors n = 20 | <2-fold: 8<br>2-3-fold: 5<br>5-10-fold: 3<br>10-20-fold: 1<br>>40-fold: 3 | 35% > 5-fold |
| Colon Tumors n = 10 | <2-fold: 9<br>>40-fold: 1 | 10% > 5-fold |
| Prostate Tumors n = 26 | <2-fold: 20<br>2-5-fold: 2<br>5-10-fold: 2<br>>10-fold: 2 | 15% > 5-fold |

Human TASK1, a Close Sequence Homolog of KCNB, is Not Overexpressed in Cancer.

TASK1 (also known as KCNK3, Duprat et al. *EMBO J.* (1997) 16, 5464-5471) shares 62% protein sequence identity with KCNB. A subset of primary breast tumors were examined to determine whether TASK is overexpressed in cancer. The level of TASK1 mRNA was determined using methodology similar to that for the determination of KCNB mRNA levels. The TASK primers and probe used for the Taqman analysis of TASK1 mRNA expression and copy number were:

```
forward PCR primer, 5' GCAGTGTCTGGAAGGCTGAAG 3'            (SEQ ID NO:12);

reverse PCR primer, 5' CGCACTG GAGGTTCAAGCTAA 3'           (SEQ ID NO:13); and, the detection probe [6-FAM]-CCTCCAGCCACATTCT CATAGCAGGTAGG-[TAMRA]   (SEQ ID NO:14).
```

TASK1 was not overexpressed in cancer nor were any breast tumors identified that exhibited an increased TASKI gene copy number (Table 3). Thus, the gene copy number increase and overexpression associated with cancer is unique to KCNB among the TASK-type K-channels.

TABLE 3

| Breast Tumor | KCNB gene copy # | Relative mRNA level KCNB | Relative mRNA level TASK1 |
|---|---|---|---|
| 95-523 | − | 1 | 0.07 |
| 95-377 | − | 3.5 | 0.9 |
| 95-326 | − | 10.0 | 0.03 |
| 94-847 | − | 2.9 | 0.3 |
| 94-797 | − | 16 | 0.7 |
| 95-347 | + | 11 | 0.03 |
| 91-82 | + | 550 | 1.8 |
| 87-634 | + | 69 | 0.7 |
| 88-682 | + | 3.5 | 0.07 |

KCNB is Highly Expressed in Normal Human Brain Tissue.

Fifteen normal human tissue total RNAs were purchased from Biochain Institute and analyzed for KCNB expression using RT-Taqman (Table 4). Most tissues express KCNB at comparable level except for brain which expresses relatively high levels of KCNB. Levels were determined relative to the level of β-actin in the tissue. The results are expressed in an arbitrary unit.

TABLE 4

| Normal tissue | Relative KCNB mRNA level |
|---|---|
| brain | 1381 |
| pancreas | 7.6 |
| heart | 8.6 |
| colon | 1.5 |
| spleen | 1.1 |
| liver | 1.2 |
| placenta | 0.91 |
| breast | 2.1 |
| kidney | 3.9 |
| stomach | 2.6 |
| ovary | 1.4 |
| lung | 2.7 |
| prostate | 0.85 |
| bladder | 2.2 |
| PBL | 0.96 |

Example 3

Expression of Functional KCNB in COS-7 Cells

The following example shows the effects of the expression of KCNB on whole cell currents.

Figure 3:
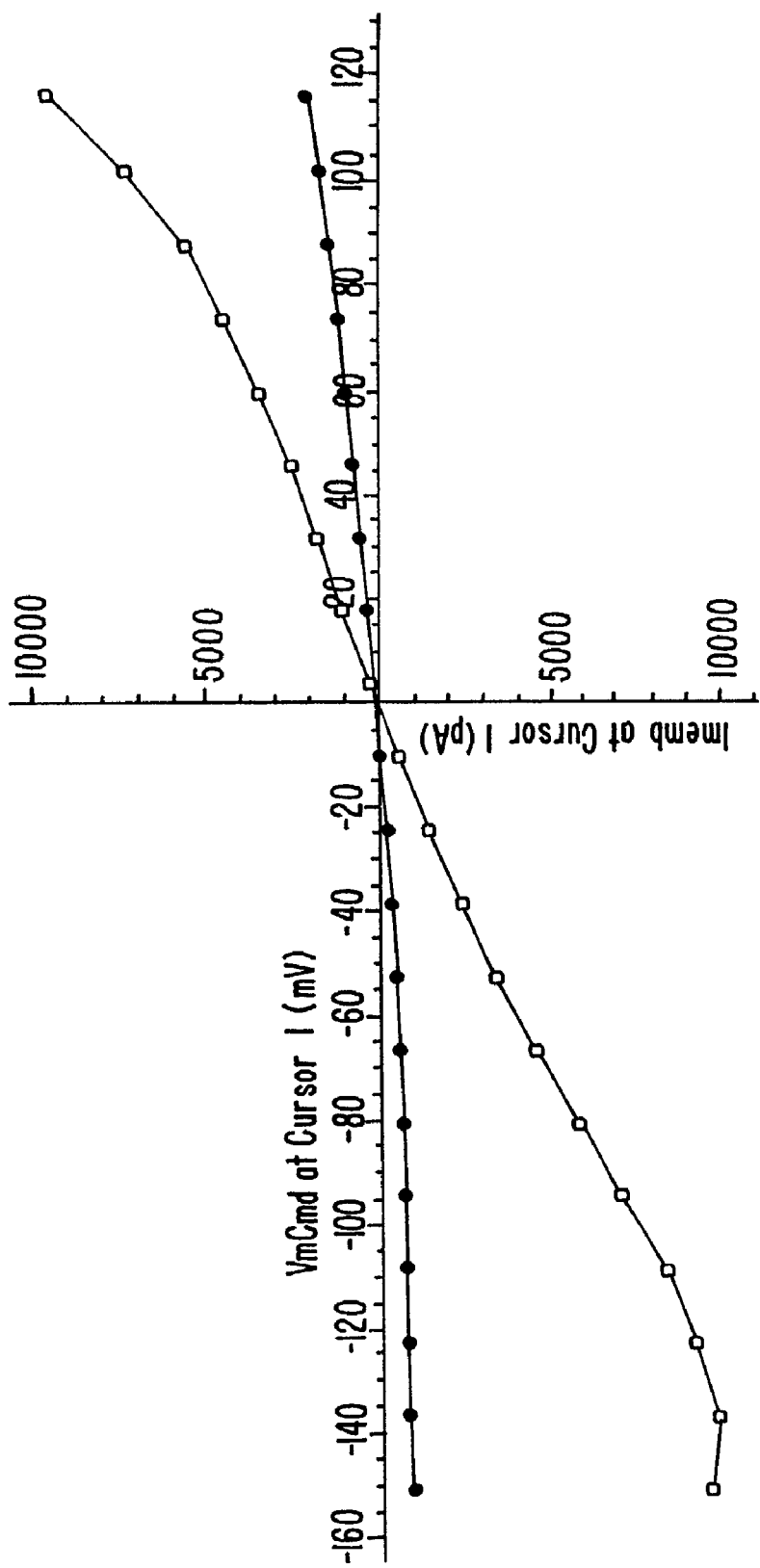
FIG. 3 illustrates the expression of functional KCNB in COS-7 cells. The squares represent the I-V curve of the KCNB-transfected cells. The closed circles represent the signal generated from the cells transfected with a plasmid control that lacks the KCNB insert.

Transfection analysis was used to examine the activity of KCNB in COS-7 cells using an expression plasmid encoding KCNB. Control cultures received the same expression vector lacking the KCNB insert. Whole cell currents were recorded in pipette and bath solutions containing 140 mM KCl. The holding potential was 0 mV, and voltage steps were from −150 to +116 mV in 14 mV increments. The results are shown in FIG. 3. The data demonstrate that currents are generated in those cells that express KCNB, and further, that KCNB exhibits an activity characteristic of a potassium channel protein.

Example 4

KCNB Protects Cells from TNF-α Induced Cell Death

Figure 4:
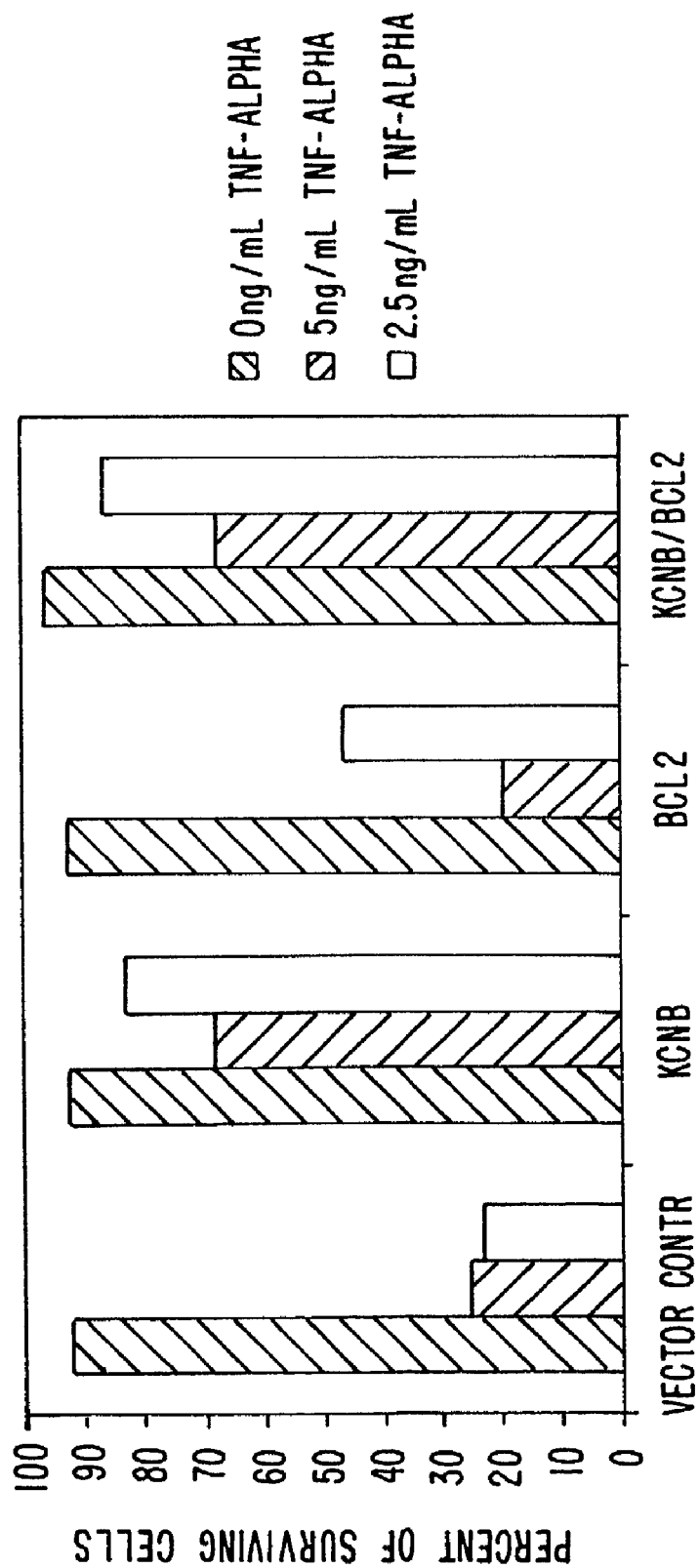
FIG. 4 illustrates the sensitivity of KCNB, BCL2, and KCNB/BCL2 transfectants to TNF-α-induced cell death.

Using a retrovirus-based gene transfer method, transfectants of MEF (mouse embryonic fibroblast) cell line A9 that expressed either KCNB, BCL2, or both KCNB and BCL2 were established. The senstivity of the these cell lines to TNF-α was then tested. The transfectants were cultured in DMEM/F-12 (Gibco)+10% FBS (Gibco) in the presence 0, 2.5, or 5 ng/ml of mouse TNF-α (Calbiochem). Forty eight hours after the addition of TNF-α, all cells, both living and dead, were collected and stained with trypan blue. The results (FIG. 4) showed that a greater number of cells that expressed KCNB or both KCNB and BCL2 survived following treatment with either 2.5 or 5 ng/ml TNF-α compared to those transfectants that were generated using the vector control or BCL2 alone. Thus, expression of KCNB was observed to protect cells from TNF-α-induced killing.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

SEQUENCE LISTING

SEQ ID NO:1
KCNB protein sequence based on a human genomic DNA sequence:

MKRQNVRTLSLIVCTFTYLLVGAAVFDALESDHEMREEEKLKAEEIRIKGKYNIS

SEDYRQLELVILQSEPHRAGVQWKFAGSFYFAITVITTIGYGHAAPGTDAGKAFC

MFYAVLGIPLTLVMFQSLGERMNTFVRYLLKRIKKCCGMRNTDVSMENMVTVG

FFSCMGTLCIGAAAFSQCEEWSFFHAYYYCFITLTTIGFGDYVALQTKGALQKKP

LYVAFSFMYILVGLTVIGAFLNLVVLRFLTMNSEDERRDAEERASLAGNRNSMVI

HIPEEPRPSRPRYKADVPDLQSVCSCTCYRSQDYGGRSVAPQNSFSAKLAPHYFH

SISYKIEEISPSTLKNSLFPSPISSISPGLHSFTDHQRLMKRRKSV

SEQ ID NO:2
Predicted KCNB open reading frame from genomic DNA:

5' ATGAAGAGGCAGAACGTGCGGACTCTGTCCCTCATCGTCTGCACCTTCACC

TACCTGCTGGTGGGCGCCGCCGTGTTCGACGCCCTCGAGTCGGACCACGAGA

TGCGCGAGGAGGAGAAACTCAAAGCCGAGGAGATCCGGATCAAGGGGAAGT

ACAACATCAGCAGCGAGGACTACCGGCAGCTGGAGCTGGTGATCCTGCAGTC

GGAACCGCACCGCGCCGGCGTCCAGTGGAAATTCGCCGGCTCCTTCTACTTTG

CGATCACGGTCATCACCACCATAGGTTATGGGCACGCTGCACCTGGCACCGA

-continued

SEQUENCE LISTING

TGCGGGCAAGGCCTTCTGCATGTTCTACGCCGTGCTGGGCATCCCGCTGACAC

TGGTCATGTTCCAGAGCCTGGGCGAGCGCATGAACACCTTCGTGCGCTACCTG

CTGAAGCGCATTAAGAAGTGCTGTGGCATGCGCAACACTGACGTGTCTATGG

AGAACATGGTGACTGTGGGCTTCTTCTCCTGCATGGGGACGCTGTGCATCGGG

GCGGCCGCCTTCTCCCAGTGTGAGGAGTGGAGCTTCTTCCACGCCTACTACTA

CTGCTTCATCACGTTGACTACCATTGGGTTCGGGGACTACGTGGCCCTGCAGA

CCAAGGGTGCCCTGCAGAAGAAGCCGCTCTACGTGGCCTTTAGCTTTATGTAT

ATCCTGGTGGGGCTGACGGTCATCGGGGCCTTCCTCAACCTGGTCGTCCTCAG

GTTCTTGACCATGAACAGTGAGGATGAGCGGCGGGATGCTGAAGAGAGGGCA

TCCCTCGCCGGAAACCGCAACAGCATGGTCATTCACATCCCTGAGGAGCCGC

GGCCCAGCCGGCCCAGGTACAAGGCGGACGTCCCGGACCTGCAGTCTGTGTG

CTCCTGCACCTGCTACCGCTCGCAGGACTATGGCGGCCGCTCGGTGGCACCGC

AGAACTCCTTCAGCGCCAAGCTTGCCCCCCACTACTTCCACTCCATCTCTTAC

AAGATCGAGGAGATCTCACCAAGCACATTAAAAAACAGCCTCTTCCCATCGC

CTATTAGCTCCATCTCTCCTGGGTTACACAGCTTTACCGACCACCAGAGGCTG

ATGAAACGCCGGAAGTCCGTTTAG 3'

SEQ ID NO:3
Sense primer for PCR amplification of KCNB cDNA:

KCNB-R5: 5'-GCCATGAAGAGGCAGAACGTGCG

SEQ ID NO:4
Anti-sense primer for PCR amplification of KCNB cDNA:

KCNB-R10: 5'-CGGACTTCCGGCGTTTCATCA

SEQ ID NO:5
Nucleotide sequence of full-length cDNA including the 5'
and 3' UTRs from breast cancer cell line ZR7530:

5' TGCGGGACATGCCCCCCGCGCCGGCTCCTTGCTGGCGGCCATGAAGAGGC

AGAACGTGCGGACTCTGTCCCTCATCGTCTGCACCTTCACCTACCTGCTGGTG

GGCGCCGCCGTGTTCGACGCCCTCGAGTCGGACCACGAGATGCGCGAGGAGG

AGAAACTCAAAGCCGAGGAGATCCGGATCAAGGGGAAGTACAACATCAGCA

GCGAGGACTACCGGCAGCTGGAGCTGGTGATCCTGCAGTCGGAACCGCACCG

CGCCGGCGTCCAGTGGAAATTCGCCGGCTCCTTCTACTTTGCGATCACGGTCA

TCACCACCATAGGTTATGGGCACGCTGCACCTGGCACCGATGCGGGCAAGGC

CTTCTGCATGTTCTACGCCGTGCTGGGCATCCCGCTGACACTGGTCATGTTCC

AGAGCCTGGGCGAGCGCATGAACACCTTCGTGCGCTACCTGCTGAAGCGCAT

TAAGAAGTGCTGTGGCATGCGCAACACTGACGTGTCTATGGAGAACATGGTG

ACTGTGGGCTTCTTCTCCTGCATGGGGACGCTGTGCATCGGGGCGGCCGCCTT

CTCCCAGTGTGAGGAGTGGAGCTTCTTCCACGCCTACTACTACTGCTTCATCA

CGTTGACTACCATTGGGTTCGGGGACTACGTGGCCCTGCAGACCAAGGGCGC

CCTGCAGAAGAAGCCGCTCTACGTGGCCTTTAGCTTTATGTATATCCTGGTGG

GGCTGACGGTCATCGGGGCCTTCCTCAACCTGGTCGTCCTCAGGTTCTTGACC

```
ATGAACAGTGAGGATGAGCGGCGGGATGCTGAAGAGAGGGCATCCCTCGCC

GGAAACCGCAACAGCATGGTCATTCACATCCCTGAGGAGCCGCGGCCCAGCC

GGCCCAGGTACAAGGCGGACGTCCCGGACCTGCAGTCTGTGTGCTCCTGCAC

CTGCTACCGCTCGCAGGACTATGGCGGCCGCTCGGTGGCACCGCAGAACTCC

TTCAGCGCCAAGCTTGCCCCCACTACTTCCACTCCATCTCTTACAAGATCGA

GGAGATCTCACCAAGCACATTAAAAAACAGCCTCTTCCCATCGCCTATTAGCT

CCATCTCTCCTGGGTTACACAGCTTTACCGACCACCAGAGGCTGATGAAACGC

CGGAAGTCCGTTTAGGTGTGGGGAGGGAAATGGGACAGAAAAGTCATTTGTC

ATAGTTGGTGTTAATTTCCATTGGTCCAACTCGTCTTTTCTTATTTATTTATTAT

TATTATTGTCATCATTATTACTTTCTCTCCTTCCTCCTTTCTTGGTCTCTTGGTC

TCATTTTCCCCCACCTTTCCAGCCAGACAGAGCAGGCCAAAGGGAAATACAG

GCCCATCCTCCTCTGAAACTCACATCTGAGCATGAAGCATGGATCTCCTCCTT

CCTTCCCAGCAGACTATGCCTTACATTTCTCACCCCACCCACCCCATCATCTCT

GCAGTGGTTTTCCCGGGACAGATGTGAGACCAAGACCACGGAGACAGAGCTG

AGAGGATACCCACCCCAAAGCTGCACATCACGCTCAGCCTTCAATCGCCTAC

CCTTAGTGGTGTCTCTGACCTAACTCCTTTCTCTTTTCCTAAGGACTGAGTGAC

TGTGTGTGTGTTGTGTGTGCTTCTGTGTGCACGTGTGTCGTGACAAAACGG

GAAGTATTAGGTATTCCGTTTTCTTTCCCATCACACATCATAGCCTGCTTTTGG

CTGCTTCCAAACAAAACGGGAAGACAAAACCCACAAGGTTTTTGATTTATCG

TATTTTGCCAAATCAAGCATGTTTCATTAAGCAGTTCTTATCCCTGATGTGTCA

TGGCCATATTTTCTAAATGCTAGGTTCTAAATTATATTAATGTTTTTTAGGGGC

GGGTGGGCAAGACGACCCAAACCATCTTAGCTTGCCAGTTCAGACATTTTTTA

AAAAGCATGCACTTTGTTAAACTGGTATGCGCTATCAACAAAAAAACTAGAA

ATGGAATAATCCAAAGCCAATAACATTAACTTATAAAAGACATTTTTAATTTT

GTCACCTCCAGTTCCAACAATTTACCATGCAACTGGAATTGTCAGGGGAAAC

GGGAAAATTGTTGGAACCCCAGAGTATCTATTTCCCTCTTATTGATGATTTTG

TGCAGCACCTACCCTGCATAAATAAGAATTATAGTGTTGGAATGCTTGGGTGA

GAATGGGTATTAGTATGTGGCTGTGGTTCCTTTTCCTCATGAAAATTGACAGG

GCATTCCTCATTAAAAATACATATCTATTTCAAGAAAAAAAAAAAA 3'
```

SEQ ID NO:6
Sense primer for quantitative PCR for KCNB:

KCNB QF1: 5'-CGGCGTCCAGTGGAAATT

SEQ ID NO:7
Anti-sense primer for quantitative PCR for KCNB:

KCNB QR1: 5'-GCCCATAACCTATGGTGGTGAT

SEQ ID NO:8
KCNB probe oligonucleotide for quantitative PCR:

KCNB QP1: 5'-(6-FAM)-CCGGCTCCTTCTACTTTGCGATCACG-(TAMRA)

SEQ ID NO:9
Sense primer for quantitative PCR for KCNB:

KCNB QF3: 5'-ACCTGCTGAAGCGCATTAAGA

-continued

SEQUENCE LISTING

SEQ ID NO:10
Anti-sense primer for quantitative PCR for KCNB:

KCNB QR3: 5'-GTCACCATGTTCTCCATAGACACG

SEQ ID NO:11
KCNB probe oligonucleotide for quantitative PCR:

KCNB QP3: 5'-(6-FAM)-CAGTGTTGCGCATGCCACAGCA-(TAMRA)

SEQ ID NO:12
Forward TASK1 primer for quantitative PCR:

5' GCAGTGTCTGGAAGGCTGAAG 3'

SEQ ID NO:13
Reverse TASK1 primer for quantitative PCR:

5' CGCACTG GAGGTTCAAGCTAA 3'

SEQ ID NO:14
TASK1 probe oligonucleotide for quantitative PCR:

5'[6-FAM]-CCTCCAGCCACATTCT CATAGCAGGTAGG-[TAMRA]3'

What is claimed is:

1. An isolated nucleic acid encoding a potassium channel polypeptide that transduces a change in membrane potential, wherein the polypeptide comprises 90% or greater identity to the amino acid sequence of SEQ ID NO:1.

2. The isolated nucleic acid of claim 1, wherein the polypeptide comprises greater than 95% amino acid sequence identity to the amino acid sequence of SEQ ID NO:1.

3. The isolated nucleic acid of claim 1, wherein the nucleic acid encodes a polypeptide that specifically binds to polyclonal antibodies generated against an amino acid sequence of SEQ ID NO:1.

4. An isolated nucleic acid encoding a protein comprising an amino acid sequence of SEQ ID NO:1.

5. An isolated nucleic acid comprising a nucleotide sequence of SEQ ID NO:2 or the protein coding region set forth in SEQ ID NO:5.

6. The isolated nucleic acid of claim 1, wherein the nucleic acid is amplified by a primer pair selected from the group consisting of SEQ ID NO:6 and SEQ ID NO:7; and SEQ ID NO:9 and SEQ ID NO:10.

7. An isolated nucleic acid encoding a potassium channel polypeptide that transduces a change in membrane potential and comprises 90% or greater identity to the amino acid sequence of SEQ ID NO:1, wherein the nucleic acid selectively hybridizes under stringent hybridization conditions comprising 50% formamide, 5×SSC and 1% SDS at 42° C. and wash conditions comprising 0.2×SSC and 0.1% SDS at 65° C. to a nucleotide sequence of SEQ ID NO:2 or SEQ ID NO:5.

8. An isolated nucleic acid encoding a potassium channel polypeptide that transduces a change in membrane potential, wherein the polypeptide comprises at least 200 contiguous amino acids of the amino acid sequence of SEQ ID NO:1.

9. An isolated nucleic acid of claim 8, wherein the polypeptide comprises two pore domains and four transmembrane domains as set forth in FIG. 1.

10. An expression vector comprising the nucleic acid of claim 1, claim 4, claim 5, claim 7, or claim 8.

11. A host cell transfected with the vector of claim 10.

12. A method of making a potassium channel polypeptide, the method comprising the step of expressing the polypeptide from a recombinant expression vector comprising a nucleic acid encoding the polypeptide, wherein the amino acid sequence of the polypeptide comprises 90% or greater amino acid identity to SEQ ID NO:1 and the encoded polypeptide transduces a change in membrane potential.

13. A method of making a recombinant cell comprising a potassium channel polypeptide, the method comprising the step of transducing the cell with an expression vector comprising a nucleic acid encoding the polypeptide, wherein the amino acid sequence of the polypeptide comprises 90% or greater amino acid identity to SEQ ID NO:1 and the encoded polypeptide transduces a change in membrane potential.

14. An isolated nucleic acid, or complement thereof, comprising at least 50 contiguous nucleotides of SEQ ID NO:2 or SEQ ID NO:5.

15. An isolated nucleic acid, or complement thereof, comprising at least 100 contiguous nucleotides of SEQ ID NO:2 or SEQ ID NO:5.

* * * * *

SEQUENCE LISTING

<160> NUMBER OF SEQ ID NOS: 18

<210> SEQ ID NO 1
<211> LENGTH: 374
<212> TYPE: PRT
<213> ORGANISM: Homo sapiens
<220> FEATURE:
<223> OTHER INFORMATION: human KCNB (Potassium Channel expressed in Breast)

<400> SEQUENCE: 1

Met Lys Arg Gln Asn Val Arg Thr Leu Ser Leu Ile Val Cys Thr Phe
 1               5                  10                  15

Thr Tyr Leu Leu Val Gly Ala Ala Val Phe Asp Ala Leu Glu Ser Asp
            20                  25                  30

His Glu Met Arg Glu Glu Glu Lys Leu Lys Ala Glu Glu Ile Arg Ile
        35                  40                  45

Lys Gly Lys Tyr Asn Ile Ser Ser Glu Asp Tyr Arg Gln Leu Glu Leu
    50                  55                  60

Val Ile Leu Gln Ser Glu Pro His Arg Ala Gly Val Gln Trp Lys Phe
65                  70                  75                  80

Ala Gly Ser Phe Tyr Phe Ala Ile Thr Val Ile Thr Thr Ile Gly Tyr
                85                  90                  95

Gly His Ala Ala Pro Gly Thr Asp Ala Gly Lys Ala Phe Cys Met Phe
            100                 105                 110

Tyr Ala Val Leu Gly Ile Pro Leu Thr Leu Val Met Phe Gln Ser Leu
        115                 120                 125

Gly Glu Arg Met Asn Thr Phe Val Arg Tyr Leu Leu Lys Arg Ile Lys
    130                 135                 140

Lys Cys Cys Gly Met Arg Asn Thr Asp Val Ser Met Glu Asn Met Val
145                 150                 155                 160

Thr Val Gly Phe Phe Ser Cys Met Gly Thr Leu Cys Ile Gly Ala Ala

```
                    165                 170                 175
Ala Phe Ser Gln Cys Glu Glu Trp Ser Phe Phe His Ala Tyr Tyr Tyr
            180                 185                 190

Cys Phe Ile Thr Leu Thr Thr Ile Gly Phe Gly Asp Tyr Val Ala Leu
            195                 200                 205

Gln Thr Lys Gly Ala Leu Gln Lys Lys Pro Leu Tyr Val Ala Phe Ser
            210                 215                 220

Phe Met Tyr Ile Leu Val Gly Leu Thr Val Ile Gly Ala Phe Leu Asn
225                 230                 235                 240

Leu Val Val Leu Arg Phe Leu Thr Met Asn Ser Glu Asp Glu Arg Arg
                245                 250                 255

Asp Ala Glu Arg Ala Ser Leu Ala Gly Asn Arg Asn Ser Met Val
            260                 265                 270

Ile His Ile Pro Glu Glu Pro Arg Pro Ser Arg Pro Arg Tyr Lys Ala
            275                 280                 285

Asp Val Pro Asp Leu Gln Ser Val Cys Ser Cys Thr Cys Tyr Arg Ser
            290                 295                 300

Gln Asp Tyr Gly Gly Arg Ser Val Ala Pro Gln Asn Ser Phe Ser Ala
305                 310                 315                 320

Lys Leu Ala Pro His Tyr Phe His Ser Ile Ser Tyr Lys Ile Glu Glu
                325                 330                 335

Ile Ser Pro Ser Thr Leu Lys Asn Ser Leu Phe Pro Ser Pro Ile Ser
            340                 345                 350

Ser Ile Ser Pro Gly Leu His Ser Phe Thr Asp His Gln Arg Leu Met
            355                 360                 365

Lys Arg Arg Lys Ser Val
        370
```

<210> SEQ ID NO 2
<211> LENGTH: 1125
<212> TYPE: DNA
<213> ORGANISM: Homo sapiens
<220> FEATURE:
<223> OTHER INFORMATION: preducted KCNB open reading frame from genomic
      DNA

<400> SEQUENCE: 2

```
atgaagaggc agaacgtgcg gactctgtcc ctcatcgtct gcaccttcac ctacctgctg     60
gtgggcgccg ccgtgttcga cgccctcgag tcggaccacg agatgcgcga ggaggagaaa    120
ctcaaagccg aggagatccg gatcaagggg aagtacaaca tcagcagcga ggactaccgg    180
cagctggagc tggtgatcct gcagtcggaa ccgcaccgcg ccggcgtcca gtggaaattc    240
gccggctcct tctactttgc gatcacggtc atcaccacca taggttatgg cacgctgca     300 cctggcaccg atgcgggcaa ggccttctgc atgttctacg ccgtgctggg catcccgctg    360
acactggtca tgttccagag cctgggcgag cgcatgaaca ccttcgtgcg ctacctgctg    420
aagcgcatta gaagtgctg tggcatgcgc aacactgacg tgtctatgga aacatggtg    480 actgtgggct tcttctcctg catggggacg ctgtgcatcg ggcggccgc cttctcccag    540 tgtgaggagt ggagcttctt ccacgcctac tactactgct tcatcacgtt gactaccatt    600
gggttcgggg actacgtggc cctgcagacc aagggtgccc tgcagaagaa gccgctctac    660
gtggccttta gctttatgta tatcctggtg gggctgacgg tcatcggggc cttcctcaac    720
ctggtcgtcc tcaggttctt gaccatgaac agtgaggatg agcggcggga tgctgaagag    780
agggcatccc tcgccggaaa ccgcaacagc atggtcattc acatccctga ggagccgcgg    840
```

```
cccagccggc ccaggtacaa ggcggacgtc ccggacctgc agtctgtgtg ctcctgcacc      900
tgctaccgct cgcaggacta tggcggccgc tcggtggcac cgcagaactc cttcagcgcc      960
aagcttgccc cccactactt ccactccatc tcttacaaga tcgaggagat ctcaccaagc     1020
acattaaaaa acagcctctt cccatcgcct attagctcca tctctcctgg gttacacagc     1080
tttaccgacc accagaggct gatgaaacgc cggaagtccg tttag                     1125

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:sense primer
      for PCR amplification of KCNB cDNA

<400> SEQUENCE: 3
gccatgaaga ggcagaacgt gcg                                               23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence:anti-sense
      primer for PCR amplification of KCNB cDNA

<400> SEQUENCE: 4
cggacttccg gcgtttcatc a                                                 21

<210> SEQ ID NO 5
<211> LENGTH: 2312
<212> TYPE: DNA
<213> ORGANISM: Homo sapiens
<220> FEATURE:
<223> OTHER INFORMATION: full length cDNA including 5' and 3' UTRs from
      breast cancer cell line ZR7530
<221> NAME/KEY: CDS
<222> LOCATION: (41)..(1165)
<223> OTHER INFORMATION: human KCNB (Potassium Channel expressed in
      Breast)

<400> SEQUENCE: 5
tgcgggacat gccccccgcg ccggctcctt gctggcggcc atgaagaggc agaacgtgcg       60
gactctgtcc ctcatcgtct gcaccttcac ctacctgctg gtgggcgccg ccgtgttcga      120
cgccctcgag tcggaccacg agatgcgcga ggaggagaaa ctcaaagccg aggagatccg      180
gatcaagggg aagtacaaca tcagcagcga ggactaccgg cagctggagc tggtgatcct      240
gcagtcggaa ccgcaccgcg ccggcgtcca gtggaaattc gccggctcct tctactttgc      300
gatcacggtc atcaccacca taggttatgg gcacgctgca cctggcaccg atgcgggcaa      360
ggccttctgc atgttctacg ccgtgctggg catcccgctg acactggtca tgttccagag      420
cctgggcgag cgcatgaaca ccttcgtgcg ctacctgctg aagcgcatta agaagtgctg      480
tggcatgcgc aacactgacg tgtctatgga aacatggtg actgtgggct tcttctcctg      540
catggggacg ctgtgcatcg ggcggccgc cttctcccag tgtgaggagt ggagcttctt      600
ccacgcctac tactactgct tcatcacgtt gactaccatt gggttcgggg actacgtggc      660
cctgcagacc aagggcgccc tgcagaagaa gccgctctac gtggcctttta gctttatgta      720 tatcctggtg gggctgacgg tcatcgggc cttcctcaac ctggtcgtcc tcaggttctt      780
gaccatgaac agtgaggatg agcggcggga tgctgaagag agggcatccc tcgccggaaa      840
```

```
ccgcaacagc atggtcattc acatccctga ggagccgcgg cccagccggc ccaggtacaa    900
ggcggacgtc ccggacctgc agtctgtgtg ctcctgcacc tgctaccgct cgcaggacta    960
tggcggccgc tcgtggcac cgcagaactc cttcagcgcc aagcttgccc ccactactt    1020
ccactccatc tcttacaaga tcgaggagat ctcaccaagc acattaaaaa acagcctctt   1080
cccatcgcct attagctcca tctctcctgg gttacacagc tttaccgacc accagaggct   1140
gatgaaacgc cggaagtccg tttaggtgtg gggagggaaa tgggacagaa aagtcatttg   1200
tcatagttgg tgttaattc cattggtcca actcgtcttt tcttatttat ttattattat   1260
tattgtcatc attattactt tctctccttc ctcctttctt ggtctcttgg tctcattttc   1320
ccccaccttt ccagccagac agagcaggcc aaagggaaat acaggcccat cctcctctga   1380
aactcacatc tgagcatgaa gcatggatct cctccttcct tcccagcaga ctatgcctta   1440
catttctcac cccacccacc ccatcatctc tgcagtggtt ttcccgggac agatgtgaga   1500
ccaagaccac ggagacagag ctgagaggat acccacccca aagctgcaca tcacgctcag   1560
ccttcaatcg cctaccctta gtggtgtctc tgacctaact cctttctctt ttcctaagga   1620
ctgagtgact gtgtgtgtgt tgtgtgtgtg cttctgtgtg cacgtgtgtc gtgacaaaac   1680
gggaagtatt aggtattccg ttttctttcc catcacacat catagcctgc ttttggctgc   1740
ttccaaacaa aacgggaaga caaaacccac aaggttttg atttatcgta ttttgccaaa    1800
tcaagcatgt ttcattaagc agttcttatc cctgatgtgt catggccata ttttctaaat   1860
gctaggttct aaattatatt aatgttttt aggggcgggt gggcaagacg acccaaacca    1920
tcttagcttg ccagttcaga catttttta aaagcatgca ctttgttaaa ctggtatgcg    1980
ctatcaacaa aaaactaga aatggaataa tccaaagcca ataacattaa cttataaaag   2040
acatttttaa ttttgtcacc tccagttcca acaatttacc atgcaactgg aattgtcagg   2100
ggaaacggga aaattgttgg aaccccagag tatctatttc cctcttattg atgatttgt    2160
gcagcaccta ccctgcataa ataagaatta tagtgttgga atgcttgggt gagaatgggt   2220
attagtatgt ggctgtggtt ccttttcctc atgaaaattg acagggcatt cctcattaaa   2280
aatacatatc tatttcaaga aaaaaaaaaa aa                                  2312

<210> SEQ ID NO 6
<211> LENGTH: 18
<212> TYPE: DNA
<213> ORGANISM: Artificial Sequence
<220> FEATURE:
<223> OTHER INFORMATION: Description of Artificial Sequence:sense primer
      KCNB QF1 for quantitative PCR for KCNB

<400> SEQUENCE: 6
cggcgtccag tggaaatt                                                   18

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence:anti-sense
      primer KCNB QR1 for quantitative PCR for KCNB

<400> SEQUENCE: 7
gcccataacc tatggtggtg at                                              22

<210> SEQ ID NO 8
```

```
<211> LENGTH: 26
<212> TYPE: DNA
<213> ORGANISM: Artificial Sequence
<220> FEATURE:
<223> OTHER INFORMATION: Description of Artificial Sequence:KCNB QP1
      probe oligonucleotide for quantitative PCR
<221> NAME/KEY: modified_base
<222> LOCATION: (1)
<223> OTHER INFORMATION: n = c modified by 6-FAM
<221> NAME/KEY: modified_base
<222> LOCATION: (26)
<223> OTHER INFORMATION: n = g modified by TAMRA

<400> SEQUENCE: 8
ncggctcctt ctactttgcg atcacn                                               26

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence:KCNB QF3
      sense primer for quantitative PCR for KCNB

<400> SEQUENCE: 9
acctgctgaa gcgcattaag a                                                    21

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:KCNB QR3
      anti-sense primer for quantitative PCR for KCNB

<400> SEQUENCE: 10
gtcaccatgt tctccataga cacg                                                 24

<210> SEQ ID NO 11
<211> LENGTH: 22
<212> TYPE: DNA
<213> ORGANISM: Artificial Sequence
<220> FEATURE:
<223> OTHER INFORMATION: Description of Artificial Sequence:KCNB QP3
      probe oligonucleotide for quantitative PCR
<221> NAME/KEY: modified_base
<222> LOCATION: (1)
<223> OTHER INFORMATION: n = c modified by 6-FAM
<221> NAME/KEY: modified_base
<222> LOCATION: (22)
<223> OTHER INFORMATION: n = a modified by TAMRA

<400> SEQUENCE: 11
nagtgttgcg catgccacag cn                                                   22

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence:forward
      TASK1 primer for quantitative PCR

<400> SEQUENCE: 12
gcagtgtctg gaaggctgaa g                                                    21

<210> SEQ ID NO 13
<211> LENGTH: 21
<212> TYPE: DNA
```

```
<213> ORGANISM: Artificial Sequence
<220> FEATURE:
<223> OTHER INFORMATION: Description of Artificial Sequence:reverse
      TASK1 primer for quantitative PCR

<400> SEQUENCE: 13
cgcactggag gttcaagcta a                                              21

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:TASK1
      detection probe oligonucleotide for quantitative PCR
<221> NAME/KEY: modified_base
<222> LOCATION: (1)
<223> OTHER INFORMATION: n = c modified by 6-FAM
<221> NAME/KEY: modified_base
<222> LOCATION: (29)
<223> OTHER INFORMATION: n = g modified by TAMRA

<400> SEQUENCE: 14
nctccagcca cattctcata gcaggtagn                                      29

<210> SEQ ID NO 15
<211> LENGTH: 394
<212> TYPE: PRT
<213> ORGANISM: Homo sapiens
<220> FEATURE:
<223> OTHER INFORMATION: human potassium channel KCNK3 (TASK1)

<400> SEQUENCE: 15

Met Lys Arg Gln Asn Val Arg Thr Leu Ala Leu Ile Val Cys Thr Phe
  1               5                  10                  15

Thr Tyr Leu Leu Val Gly Ala Ala Val Phe Asp Ala Leu Glu Ser Glu
                 20                  25                  30

Pro Glu Leu Ile Glu Arg Gln Arg Leu Glu Leu Arg Gln Gln Glu Leu
             35                  40                  45

Arg Ala Arg Tyr Asn Leu Ser Gln Gly Gly Tyr Glu Glu Leu Glu Arg
         50                  55                  60

Val Val Leu Arg Leu Lys Pro His Lys Ala Gly Val Gln Trp Arg Phe
 65                  70                  75                  80

Ala Gly Ser Phe Tyr Phe Ala Ile Thr Val Ile Thr Thr Ile Gly Tyr
                 85                  90                  95

Gly His Ala Ala Pro Ser Thr Asp Gly Gly Lys Val Phe Cys Met Phe
            100                 105                 110

Tyr Ala Leu Leu Gly Ile Pro Leu Thr Leu Val Met Phe Gln Ser Leu
            115                 120                 125

Gly Glu Arg Ile Asn Thr Leu Val Arg Tyr Leu Leu His Arg Ala Lys
        130                 135                 140

Lys Gly Leu Gly Met Arg Arg Ala Asp Val Ser Met Ala Asn Met Val
145                 150                 155                 160

Leu Ile Gly Phe Phe Ser Cys Ile Ser Thr Leu Cys Ile Gly Ala Ala
                165                 170                 175

Ala Phe Ser His Tyr Glu His Trp Thr Phe Phe Gln Ala Tyr Tyr Tyr
            180                 185                 190

Cys Phe Ile Thr Leu Thr Thr Ile Gly Phe Gly Asp Tyr Val Ala Leu
            195                 200                 205

Gln Lys Asp Gln Ala Leu Gln Thr Gln Pro Gln Tyr Val Ala Phe Ser
        210                 215                 220
```

```
Phe Val Tyr Ile Leu Thr Gly Leu Thr Val Ile Gly Ala Phe Leu Asn
225                 230                 235                 240

Leu Val Val Leu Arg Phe Met Thr Met Asn Ala Glu Asp Glu Lys Arg
            245                 250                 255

Asp Ala Glu His Arg Ala Leu Leu Thr Arg Asn Gly Gln Ala Gly Gly
        260                 265                 270

Gly Gly Gly Gly Gly Ser Ala His Thr Thr Asp Thr Ala Ser Ser Thr
    275                 280                 285

Ala Ala Ala Gly Gly Gly Gly Phe Arg Asn Val Tyr Ala Glu Val Leu
    290                 295                 300

His Phe Gln Ser Met Cys Ser Cys Leu Trp Tyr Lys Ser Arg Glu Lys
305                 310                 315                 320

Leu Gln Tyr Ser Ile Pro Met Ile Ile Pro Arg Asp Leu Ser Thr Ser
                325                 330                 335

Asp Thr Cys Val Glu Gln Ser His Ser Ser Pro Gly Gly Gly Gly Arg
            340                 345                 350

Tyr Ser Asp Thr Pro Ser Arg Arg Cys Leu Cys Ser Gly Ala Pro Arg
        355                 360                 365

Ser Ala Ile Ser Ser Val Ser Thr Gly Leu His Ser Leu Ser Thr Phe
    370                 375                 380

Arg Gly Leu Met Lys Arg Arg Ser Ser Val
385                 390

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence:6-His
      epitope tag

<400> SEQUENCE: 16

His His His His His His
 1               5

<210> SEQ ID NO 17
<211> LENGTH: 8
<212> TYPE: PRT
<213> ORGANISM: Artificial Sequence
<220> FEATURE:
<223> OTHER INFORMATION: Description of Artificial Sequence:
      anti-DYKDDDDK epitope tag

<400> SEQUENCE: 17

Asp Tyr Lys Asp Asp Asp Asp Lys
 1               5

<210> SEQ ID NO 18
<211> LENGTH: 200
<212> TYPE: PRT
<213> ORGANISM: Artificial Sequence
<220> FEATURE:
<223> OTHER INFORMATION: Description of Artificial Sequence:poly-Gly
      linker
<221> NAME/KEY: MOD_RES
<222> LOCATION: (6)..(200)
<223> OTHER INFORMATION: Gly at positions 6-200 may be present or absent

<400> SEQUENCE: 18

Gly Gly Gly Gly Gly Gly Gly Gly Gly Gly Gly Gly Gly Gly Gly
 1               5                  10                  15
```

-continued

```
Gly Gly Gly Gly Gly Gly Gly Gly Gly Gly Gly Gly Gly Gly Gly
            20                  25                  30
Gly Gly Gly Gly Gly Gly Gly Gly Gly Gly Gly Gly Gly Gly Gly
            35                  40                  45
Gly Gly Gly Gly Gly Gly Gly Gly Gly Gly Gly Gly Gly Gly Gly
    50                  55                  60
Gly Gly Gly Gly Gly Gly Gly Gly Gly Gly Gly Gly Gly Gly Gly
65                  70                  75                  80
Gly Gly Gly Gly Gly Gly Gly Gly Gly Gly Gly Gly Gly Gly Gly
                85                  90                  95
Gly Gly Gly Gly Gly Gly Gly Gly Gly Gly Gly Gly Gly Gly Gly
            100                 105                 110
Gly Gly Gly Gly Gly Gly Gly Gly Gly Gly Gly Gly Gly Gly Gly
        115                 120                 125
Gly Gly Gly Gly Gly Gly Gly Gly Gly Gly Gly Gly Gly Gly Gly
    130                 135                 140
Gly Gly Gly Gly Gly Gly Gly Gly Gly Gly Gly Gly Gly Gly Gly
145                 150                 155                 160
Gly Gly Gly Gly Gly Gly Gly Gly Gly Gly Gly Gly Gly Gly Gly
                165                 170                 175
Gly Gly Gly Gly Gly Gly Gly Gly Gly Gly Gly Gly Gly Gly Gly
            180                 185                 190
Gly Gly Gly Gly Gly Gly Gly Gly
        195                 200
```